United States Patent [19]
Mulligan et al.

[11] Patent Number: 6,001,350
[45] Date of Patent: Dec. 14, 1999

[54] GENETIC MODIFICATION OF ENDOTHELIAL CELLS

[76] Inventors: Richard C. Mulligan, 2 Sandy Pond Rd., Lincoln, Mass. 01773; Lawrence K. Cohen, 5670 Cabot Dr., Oakland, Calif. 94611; Louis K. Birinyi, 74 Moss Hill Rd., Boston, Mass. 02131; James M. Wilson, 3686 Riverpines Dr., Ann Arbor, Mich. 48103

[21] Appl. No.: 08/488,420

[22] Filed: Jun. 7, 1995

Related U.S. Application Data

[63] Continuation of application No. 08/249,092, May 25, 1994, Pat. No. 5,674,722, which is a continuation of application No. 07/786,188, Oct. 31, 1991, abandoned, which is a continuation-in-part of application No. 07/607,252, Oct. 31, 1990, abandoned, which is a continuation-in-part of application No. 07/131,926, Dec. 11, 1987, abandoned.

[51] Int. Cl.⁶ .............................. A61K 48/00; C12N 5/10
[52] U.S. Cl. ........................................ 424/93.21; 435/375
[58] Field of Search .............................. 435/240.2, 240.1, 435/172.3, 240.23, 240.243, 375; 424/93.21, 93.2; 604/891.1; 623/1

[56] References Cited

U.S. PATENT DOCUMENTS

| | | | |
|---|---|---|---|
| 4,980,286 | 12/1990 | Morgan et al. | 435/172.3 |
| 5,399,346 | 3/1995 | Anderson et al. | 424/93.21 |

FOREIGN PATENT DOCUMENTS

| | | |
|---|---|---|
| WO 8905345 | 6/1989 | WIPO . |
| WO 8907136 | 8/1989 | WIPO . |
| WO 9002806 | 3/1990 | WIPO . |
| WO 9006997 | 6/1990 | WIPO . |

OTHER PUBLICATIONS

Ledley, F.D., "Clinical Considerations in the Design of Protocols for Somatic Gene Therapy", *Human Gene Therapy* 2:77–83 (191).
Dichek, D.A., "Retroviral Vector–mediated Gene Transfer into Endothelial Cells", *Mol. Biol. Med.* 8:257–266 (1991).
Gilboa, E., "Retrovirus Vectors and Their Uses in Molecular Biology", *BioEssay* 5(6):252–257 (1987).
Yeager et al., "New Graft Materials and Current Approaches to an Acceptable Small Diameter Vascular Graft", *Trans. Am. Soc. Artif. Intern. Organs* 34:88–94 (1988).
Bender et al., "Evidence that the packaging signal of Moloney murine leukemia virus extends into the gag region", *J. Virol.* 61(5):1639–1646 (1987).
Yu, S.F. et al., "Self inactivating retroviral vectors designed for transfer of whole genes into mammalian cells", *Proc. Natl. Academy of Sci.* 83(10):3194–3198 (1986).
Cone, R.D. et al., Regulated expression of a complete human beta–globulin gene encoded by a transmissable retrovirus vector, *Mol. Cell. Biol.*, vol. 7(2):887–897 (1987).
Lewis, L.J. et al., "Replication of human endothelial cells in culture", *Science* 181(98):453–454 (1973).
Foxall, T.L. et al., "Adult Human Endothelial Cell Coverage of small–caliber dacron and polytetrafluoroethylene vascular prosthesis in–vitro", *J. Surg. Res.*, 41(2):158–172 (1986).
Connors, R.W. et al., "DHFR coamplification of t–PA in DHFR+ bovine endothelial cells: in vitro characterization of the purified serine protease", *DNA*, 7(9):651–61 (1988).
Wilson, J.M. et al., "Implantation of vascular grafts lined with genetically modified endothelial cells", *Science*, 244:1344–46 (1989).
Zwiebel, J.A. et al., "High–level recombinant gene expression in rabbit endothelial cells transduced by retroviral vectors", *Science*, 243:220–222 (1989).
Cepko, C.L. et al., "Construction and applications of a highly transmissable murine retrovirus shuttle vector", *Cell*, 37(3):1053–62 (1984).
Lim et al., "Retro–virus–mediated transfer of human adenosine deaminase: expression of functional enzyme in murine hematopoietic stem cells in vivo", *Molecular and Cellular Biology*, 7(10):3459–3465 (1987).
Wilson et al., "Correction of the genetic defect in hepatocytes from the Watanbe heritable hyperlipidemic rabbit", *PNAS USA*, 85:4421–4425 (1988).
Israel et al., "Retroviral–mediated transfer and amplification of a human factor VIII gene", *Blood*, 75:1074–1080 (1990).

*Primary Examiner*—Nancy Degen
*Assistant Examiner*—Robert Schwartzman
*Attorney, Agent, or Firm*—Pennie & Edmonds LLP

[57] ABSTRACT

Endothelial cells transduced with genetic material encoding a polypeptide or protein of interest and, optionally, a selectable marker, as well as methods for making and using the transduced endothelial cells are disclosed. Such endothelial cells are useful in improving the performance of vascular grafts and in delivering the encoded polypeptide or protein, such as an enzyme, a hormone, a receptor or a drug, to an individual.

6 Claims, 22 Drawing Sheets pLJ pEm

MFG

αSGC

IMPLANTATION OF CARTOTID INTEPOSITION GRAFTS SEEDED
WITH GENETICALLY MODIFIED ENDOTHELIAL CELLS

FIG. 9A
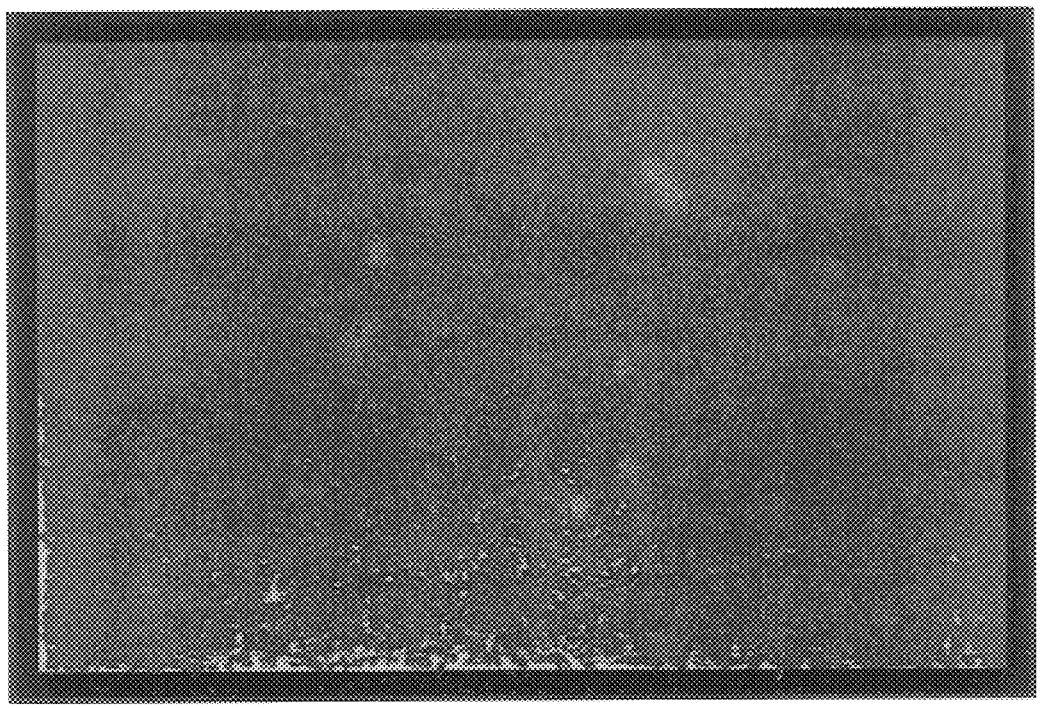
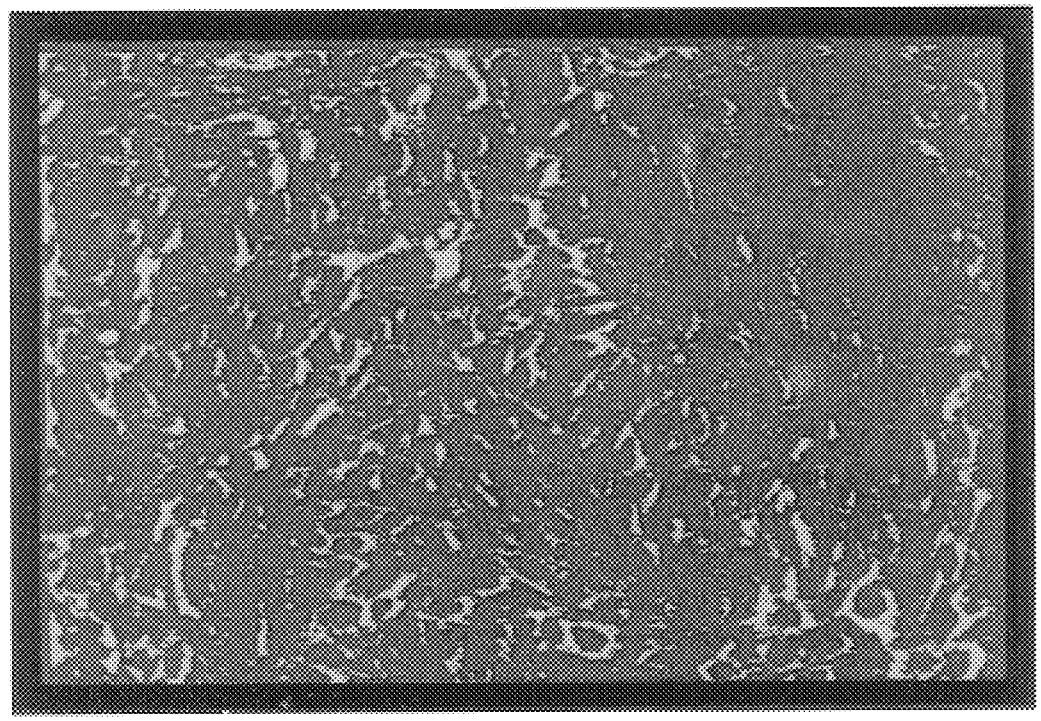
FIG. 9B

GENETIC MODIFICATION OF ENDOTHELIAL CELLS

This is a continuation of application Ser. No. 08/249,092, filed May 25, 1994, U.S. Pat. No. 5,674,722, which is a continuation of application Ser. No. 07/786,188 filed Oct. 31, 1991, abandoned; which is a CIP of application Ser. No. 07/607,252 filed Oct. 31, 1990, abandoned which is a CIP of application Ser. No. 07/131,926 filed Dec. 11, 1987, abandoned.

DESCRIPTION

1. Sponsorship

Work described herein was supported by grants from the National Institutes of Health, the Howard Hughes Medical Institute, and the Whitehead Institute for Biomedical Research.

2. Background

The endothelium is a single layer of flattened transparent cells which are joined edge to edge, with the result that they form a membrane of cells. Endothelial cells originate during development from the embryonic mesoblast or mesoderm. They occur on the free surfaces of serous membranes, in the anterior chamber of the eye and on the surface of the brain and spinal cord. In addition, they form the lining membrane of the heart, blood vessels, and lymphatics.

It is possible, using methods developed in recent years, to attain interspecies genetic recombination. Genes derived from different biological classes are able to replicate and be expressed in a selected microorganism. Therefore, it is possible to introduce into a microorganism genes specifying a metabolic or synthetic function (e.g., hormone synthesis, protein synthesis, nitrogen fixation) which is characteristic of other classes of organisms by linking the genes to a particular viral or plasmid replicon.

Since the late 1970s, progress has been made toward the development of general methods for introducing cloned DNA sequences into mammalian cells. At the present time, however, there is a need for an effective method of stably introducing selected genetic material of interest into endothelial cells and enabling them to express it, thus producing the encoded protein or polypeptide.

SUMMARY OF THE INVENTION

The invention described herein relates to genetically engineered endothelial cells and particularly to genetically engineered endothelial cells which express selected genetic material of interest (DNA or RNA) which has been incorporated into them, for example by means of a retroviral vector having a recombinant genome which includes the genetic material of interest. It also relates to methods of stably introducing into endothelial cells such genetic material and methods of using the genetically engineered endothelial cells.

Endothelial cells of this invention have stably incorporated in them genetic material of interest, which encodes a product (e.g. , a protein, polypeptide, or functional RNA) whose production in the endothelial cells is desired. The modified endothelial cells express the incorporated genetic material (produce the encoded product). This genetic material of interest is referred to herein as incorporated genetic material. The incorporated genetic material can be any selected DNA of interest (e.g., all or a portion of a gene encoding a product of interest) or RNA of interest. It can be, for example, DNA or RNA which is present in and expressed by normal endothelial cells; DNA or RNA which does not normally occur in endothelial cells; DNA or RNA which normally occurs in endothelial cells but is not expressed in them at levels which are biologically significant (i.e., levels sufficient to produce the normal physiological effects of the protein or the polypeptide it encodes); DNA or RNA which occurs in endothelial cells and has been modified so that it is expressed in endothelial cells; and any DNA or RNA which can be modified to be expressed in endothelial cells, alone or in any combination thereof. Endothelial cells of the present invention can also express genetic material encoding a selectable marker, thus providing a means by which cells expressing the incorporated genetic material are identified and selected for in vitro. Endothelial cells containing incorporated genetic material are referred to as transduced endothelial cells.

In particular, retroviral vectors have been used to stably transduce endothelial cells with genetic material which includes genetic material encoding a polypeptide or protein of interest not normally expressed at biologically significant levels in endothelial cells. The genetic material introduced in this manner can also include genetic material encoding a dominant selectable marker. Genetic material including DNA encoding a polypeptide of interest alone or DNA encoding a polypeptide of interest and a dominant selectable marker has been introduced into cultured endothelial cells. Expression of these genes by the endothelial cells into which they have been incorporated (i.e., endothelial cells transduced by the use of retroviral vectors) has also been demonstrated.

Because genes can be introduced into endothelial cells using a retroviral vector, they can be "on" (subject to) the retroviral vector control; in such a case, the gene of interest is transcribed from a retroviral promoter. Alternatively, retroviral vectors having additional promoter elements (in addition to the promoter incorporated in the recombinant retrovirus) which are responsible for the transcription of the genetic material of interest, can be used. For example, a construct in which there is an additional promoter modulated by an external factor or cue can be used, making it possible to control the level of polypeptide being produced by the endothelial cells by activating that external factor or cue. For example, heat shock proteins are proteins encoded by genes in which the promoter is regulated by temperature. The promoter of the gene which encodes the metal-containing protein metallothionine is responsive to cadmium (Cd++) ions. Incorporation of this promoter or another promoter influenced by external cues also makes it possible to regulate the production of the polypeptide by the engineered endothelial cells.

Endothelial cells may be transduced in two general settings in vitro or in vivo. Both settings require the use of a method for the transfer of genetic material of interest into endothelial cells, such as through use of a recombinant retroviral vector or other vector. For in vitro transduction, endothelial cells grown in tissue culture vessels are exposed to a vector, such as a recombinant retrovirus encoding the genetic material of interest, thereby producing transduced endothelial cells. Endothelial cells transduced in vitro with the genetic material are then transplanted using one of a variety of known methods. Such methods include, but are not limited to, the transplantation of synthetic vessels or prosthetic valves lined with transduced endothelial cells or the transplantation of a device or matrix designed to house transduced endothelial cells.

Alternatively, the transduction can be performed in vivo by applying the method for transfer of genetic material of interest to endothelial cells in a tissue or organ. For in vivo transduction, endothelial cells present in a tissue or organ are exposed, for example, to a recombinant retrovirus encoding the genetic material of interest. Such methods include, but are not limited to, the site directed administration of recombinant retrovirus into a specific organ, limb, or blood vessel (e.g., via a catheter). Unlike endothelial cells transduced in vitro, these endothelial cells transduced in vivo would not require methods for their subsequent transplantation.

A method of transplanting endothelial cells transduced in vitro is also a subject of the present invention. Endothelial cells which have been transduced in vitro are particularly useful for improving prosthetic implants (e.g., vessels made of synthetic materials such as Dacron and Gortex.) which are used in vascular reconstructive surgery. For example, prosthetic arterial grafts are often used to replace diseased arteries which perfuse vital organs or limbs. However, the currently available grafts are usually made of synthetic material and are subject to many complications, the worst of which is a high rate of re-stenosis or occlusion. Animal studies suggest that lining the graft with autologous endothelial cells prior to implantation may decrease, but not prevent, graft reocclusion with its attendant morbid consequences.

However, endothelial cells can be modified according to the method of the present invention in a way that improves their performance in the context of an implanted graft. Examples include secretion or expression of a thrombolytic agent to prevent intraluminal clot formation, secretion of an inhibitor of smooth muscle proliferation to prevent luminal stenosis due to smooth muscle hypertrophy, and expression and/or secretion of an endothelial cell mitogen or autocrine factor to stimulate endothelial cell proliferation and improve the extent or duration of the endothelial cell lining of the graft lumen.

For a similar application, endothelial cells of the present invention can also be used to cover the surface of prosthetic heart valves to decrease the risk of the formation of emboli by making the valve surface less thrombogenic.

Endothelial cells transduced by the method of the subject invention or a vascular implant lined with transduced endothelial cells can also be used to provide constitutive synthesis and delivery of polypeptides or proteins, which are useful in prevention or treatment of disease. In this way, the polypeptide is secreted directly into the bloodstream of the individual. Currently available methods, in contrast, involve parenteral administration of the desired polypeptide.

In addition, there is no need for extensive (and often costly) purification of the polypeptide before it is administered to an individual, as is generally necessary with an isolated polypeptide (e.g., insulin). Endothelial cells modified according to the present invention produce the polypeptide hormone as it would normally be produced.

Another advantage to the use of genetically engineered endothelial cells is that one can target the delivery of therapeutic levels of a secreted product to a specific organ or limb. For example, a vascular implant lined with endothelial cells transduced in vitro can be grafted into a specific organ or limb; or the endothelial cells of a particular limb, organ or vessel can be transduced in vivo. The secreted product of the transduced endothelial cells will be delivered in high concentrations to the perfused tissue, thereby achieving a desired effect to a targeted anatomical location. This product will then be diluted to nontherapeutic levels in the venous circulation during its return to the heart.

Another important advantage of the delivery system of this invention is that because it is a continuous delivery system, the short half lives of hormone polypeptides is not a limitation. For example, the half life of human growth hormone (HGH) is approximately 19 minutes and parathyroid hormone, approximately 2½ to 5 minutes.

BRIEF DESCRIPTION OF THE DRAWINGS

FIG. 2a is pLJ and FIG. 2b is pEm, FIG. 2c is MFG and FIG. 2D is α-SGC.

FIG. 9A is a photograph of canine endothelial cells infected with a retrovirus that expresses tPA. A dark cytoplasmic stain is seen in those cells expressing tPA. FIG. 9b is a photograph of control cells not infected with the tPA retrovirus.

DETAILED DESCRIPTION OF THE INVENTION

Figure 1:
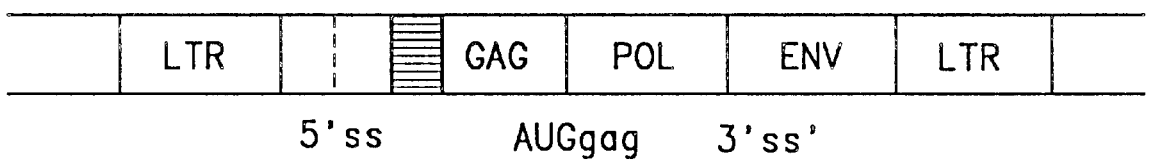
FIG. 1 is a schematic representation of a wild type murine leukemia virus (retroviral) genome.

Genetic material of interest has been incorporated into endothelial cells and expressed in the resulting genetically engineered endothelial cells. Genetic material of interest incorporated into endothelial cells according to the method described can be any selected DNA of interest (e.g., all or a portion of a gene encoding a product of interest) or any selected gene encoding a product of interest) or any selected RNA of interest. For example, it can be DNA or RNA which is present and expressed in normal endothelial cells; DNA or RNA which does not normally occur in endothelial cells; DNA or RNA which normally occurs in 2-endothelial cells but, is not expressed in them at levels which are biologically significant (levels sufficient to produce the normal physiological effect of the protein or polypeptide it encodes); DNA or RNA which occurs in endothelial cells and has been modified in such a manner that it can be expressed in such cells; and any DNA or RNA which can be modified to be expressed in endothelial cells, alone or in any combination thereof. This genetic material of interest is referred to herein as incorporated genetic material.

Endothelial cells of the present invention express the incorporated genetic material. For example, the endothelial cells of the present invention express genetic material encoding a polypeptide or a protein of interest (genetic material of interest). Endothelial cells of the present invention can also include and express a gene encoding a selectable marker. Endothelial cells which express incorporated genetic material are referred to herein as transduced endothelial cells.

Genetic material of interest which is DNA normally present in and expressed by endothelial cells can be incorporated into endothelial cells with the result that they are able to overproduce the desired protein, polypeptide, or RNA.

As described in detail herein, genetic material encoding a hormone has been introduced into endothelial cells by exposing them to media that contains a virus having a recombinant genome (i.e., by infecting them). The media used was a viral supernatant obtained by harvesting media in which recombinant virus producing cells have been grown. That is, producer cells have been grown in tissue culture to a confluent density in Dulbecco's Modified Eagle's medium (DME) with 10% calf serum (CS) and penicillin and streptomycin. Fresh media was added and subsequently (e.g., approximately 12 hours later), the media was harvested. Approximately 10 ml of media was harvested from a 10 cm plate of confluent producer cells. The harvested media (or viral stock) was filtered through a 0.45 micron Millipore filter to remove detached producer cells and was used immediately to infect cells or is stored at −70° C. Media was removed from a subconfluent plate of endothelial cells (recipient endothelial cells) and quickly replaced with viral stock (e.g., 5 ml/10 cm. plate) containing 8 mcg/ml of polybrene (Aldrich). Subsequently (e.g., approximately 12 hours later), this was removed and replaced with fresh media.

The recombinant genome of the infectious virus includes the genetic material of interest, which is incorporated into endothelial cells. The recombinant genome can also have genetic material encoding a dominant selectable marker. Transduced endothelial cells which express a polypeptide not normally expressed by such cells at biologically significant levels and, optionally, a dominant selectable marker have been made, as described herein.

The recombinant genome in one instance included genetic material encoding human parathyroid hormone (hPTH). In another instance, the recombinant genome also included a gene encoding a dominant selectable marker (e.g., the neo gene which encodes neomycin resistance in bacteria and G418 resistance in mammalian cells). As a result, the endothelial cells were transduced—that is, the genetic material of interest (in this case, DNA encoding hPTH and, optionally, the neo gene) was stably introduced into the endothelial cells. The transduced endothelial cells express the encoded hPTH alone or in addition to the neo resistance protein, resulting in cells having the selectable trait.

In another instance, the recombinant genome included only the genetic material of interest (e.g. factor VIII clotting protein or tissue plasminogen activator (tPA) and not a gene encoding a dominant selectable marker (e.g. neo gene). As a result, the transduced endothelial cells express the factor VIII protein or tPA in the absence of the dominant selectable marker gene.

As described below, endothelial cells have been transduced with genes which code for secreted products (e.g., human parathyroid hormone (hPTH) (see Example 1) tissue plasminogen activator (tPA) (see Example 5) and human clotting factor VIII protein (see Example 6); a gene which codes for a membrane receptor (e.g., low density lipoprotein receptor (LDLR) (see Example 2); and a gene coding for an intracellular bacterial enzyme (e.g., beta-galactosidase) (see Example 3).

The transduction of endothelial cells may be performed either in vitro or in vivo. For example, in vivo transduction of endothelial cells may be carried out using a recombinant retrovirus which is introduced into an individual via site directed administration of the recombinant retrovirus into a specific organ, limb or blood vessel (e.g., via a catheter, as described in Example 8). The in vivo transduction of endothelial cells has several advantages, one of which is the lack of a need for a method to transplant the transduced endothelial cells. Endothelial cells transduced in vitro are first grown in tissue culture vessels, removed from the culture vessel, and introduced into or implanted into the body.

Endothelial cells transduced in vitro can be introduced into the recipient by one of several methods. For example, transduced endothelial cells can be seeded onto the lumen of a prosthetic vessel, where they will then grow to confluence, covering the lumen of the vessel. The cells form the lining of what has been called a neointima, a well organized structure that resembles the intima and media of a native vessel (i.e., a covering of endothelial cells with deeper layers of smooth muscle cells). The feasibility of this approach has been demonstrated by experiments in which vascular grafts, seeded with autologous retrovirus-transduced endothelial cells were implanted into dogs (see Example 4).

External jugular veins harvested from adult mongrel dogs were used as a source of endothelial cells which were plated in vitro during a 10–14 day period by two serial passages. Cells from each animal were divided into two aliquots and were either infected with a replication defective retrovirus containing the reporter gene, beta-galactosidase or were mock infected. Small diameter dacron grafts were seeded at subconfluent densities with endothelial cells by the autologous clot method and surgically implanted as carotid interposition grafts into the dog from which the cells were harvested; each dog received a graft seeded with the genetically modified cells and a contralateral graft seeded with mock infected cells. Five weeks after implantation, the grafts were harvested and analyzed.

Cells were enzymatically harvested from the luminal surface of a portion of the graft to permit a more detailed characterization. Primary cultures of cells were established and expanded in vitro for approximately 2–3 weeks prior to analysis. Genetically modified endothelial cells were identified in this population by Southern analysis and by the cytochemical assay for vector-expressed betagalactosidase which is encoded by the lacZ gene.

The majority of cells (less than 95%) harvested from the graft and expanded in vitro retained differentiated endothelial function. However, the proportion of cells that expressed viral directed beta-galactosidase or contained proviral sequences was consistently decreased 2–10 fold when compared to the cultures that were analyzed at the time of seeding. This disparity is due in part to the partial repopulation of grafts with endogenous cells by growth through interstices or from the anastomoses. The transduced cells persisted on the lumen of the graft for at least five weeks and the transferred gene continued to function.

Alternatively, endothelial cells that have been transduced in vitro can be grafted onto a blood vessel in vivo through the use of a catheter. It is also possible to introduce transduced endothelial cells into body cavities which are lined by serosal membranes, such as the peritoneal cavity, the pleural space, and the pericardial space. In this case, the endothelial cells seed the serosal lining and secrete the product into the cavity. The product is then be absorbed via the lymphatic system.

Isolation of Endothelial Cells

The isolation and maintenance of endothelial cells from capillaries and large vessels (e.g., arteries, veins) of many species of vertebrates has been well described in the literature. For example, McGuire and Orkin describe a simple procedure for culturing and passaging endothelial cells from large vessels of small animals. McGuire, R. W. and R. W. Orkin, *Biotechniques,* 5:546–554 (1987).

Frequently, calf aorta is the source of endothelial cells. A typical protocol for isolation of endothelial cells from a large artery is described below. Sections of aortas freshly harvested are placed under sterile conditions, in a solution containing collagenase (e.g., 0.5 mg/ml) for 15–20 minutes at 37 C. The aortas are then rinsed twice with tissue culture medium (e.g., RPMI 1640) and the lumenal sheet of endothelial cells is removed in complete medium (RPMI containing 15 mm Hepes, pH 7.4, penicillin/streptomycin and 20% fetal calf serum) by gentle agitation, according to the method of Booyse et al. Booyse, F. M. et al., *Thrombosis Diath.*

*Haemorrh.,* 34:825–839 (1975). The cell patches are transferred to tissue culture flasks in complete medium.

The cells divide and eventually cover the plate; when the plate is confluent, the cells can be passaged using standard tissue culture techniques. The purity of the cultures is assessed by uptake of fluorescent labeled acetylated LDL which is specifically taken up by endothelial cells. If the cultures are not pure (i.e., contaminated with cells other than endothelial cells, such as smooth muscle cells or fibroblasts), endothelial cells are cloned by limiting dilution and expanded to yield pure cultures. The life span of endothelial cells is limited in culture but varies markedly, depending on the anatomical source and donor animal. Bovine aortic endothelial cells have been maintained in culture for at least 15–20 passages.

Canine endothelial cells can be isolated from explanted segments of the external jugular vein, and human cells from segments of either the umbilical or saphenous veins. All cells can be freed from the vessel wall by published procedures involving collagenase treatments which reproducibly yield pure cultures of human endothelial cells but which can produce mixed cultures of smooth muscle and endothelial cells from canine veins (Hunter, T. J. et al., *Trans. Am. Soc. Artif. Intern. Organs ,* 29:177182 (1983); Watkins, M. T. et al., *J. Surg. Res.,* 36: 588–596, 1984)). To limit the potential for smooth muscle cell overgrowth, the canine endothelial cells can be cultured in plasma-derived serum, a media supplement low in smooth muscle cell mitogens. All cultures can be monitored by immunohistochemical procedures which identify smooth muscle cells with a monoclonal antibody recognizing muscle-specific actin isoforms, and endothelial cells with an antisera which recognizes Factor VIII-related antigen (Wagner, D. D., et al., *J. Cell Biol.* 95: 355–360, 1982), as well as labeled acetylated LDL as discussed above.

Retroviral Vectors

Retroviruses are RNA viruses; that is, the viral genome is RNA. This genomic RNA is, however, reverse transcribed into a DNA copy which is integrated stably and efficiently into the chromosomal DNA of transduced cells. This stably integrated DNA copy is referred to as a provirus and is inherited by daughter cells as any other gene. As shown in FIG. 1, the wild type retroviral genome and the proviral DNA have three genes: the ~gag, the pol and the env, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs.

Adjacent to the 5' LTR are sequences necessary for reverse transcription of the genome (the tRNA primer binding site) and for efficient encapsidation of viral RNA into particles (the Psi site). Mulligan, R. C., In: *Experimental Manipulation of Gene Expression*, M. Inouye (ed), 155–173 (1983); Mann, R., et al., *Cell,* 33:153–159 (1983); Cone, R. D. and R. C. Mulligan, *Proceedings of the National Academy of Sciences,* U.S.A., 81:6349–6353 (1984).

If the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Mulligan and coworkers have described retroviral genomes from which these Psi sequences have been deleted, as well as cell lines containing the mutant genome stably integrated into the chromosome. Mulligan, R. C., In: *Experimental Manipulation of Gene Expression*, M. Inouye (ed), 155–173 (1983); Mann, R., et al., *Cell*, 33:153–159 (1983); Cone, R. D. and R. C. Mulligan, *Proceedings of the National Academy of Sciences*, U.S.A., 81:6349–6353 (1984). The teachings of these publications are incorporated herein by reference.

As described by Mulligan and coworkers, the Psi 2 cell line was constructed in the following manner: A mutant murine leukemia virus (MULV) genome in which the region or the genome implicated in the encapsidation of viral RNA into virions is deleted (the Psi sequence in FIG. 1) was constructed. This genome was stably introduced in NIH3T3 cells by DNA cotransfection and stable transfectants that produced all of the viral proteins used for encapsidation, yet budded noninfectious particles, were isolated. The mutant of MuLV was constructed by deleting 351 nucleotides from an infectious proviral DNA clone between the putative env mRNA 5' splice site and the AUG that initiates the coding sequence for Pr 65 gag. The deletion was made from a Bal I site to a Pst 1 site and a HindIII site was generated at the point of deletion.

pMOV. (pMOVPsi) was constructed as follows: Three purified DNA fragments were ligated together to construct pMOV Psi–. The first was obtained by digesting pMOV Psi+ with Xho I to completion, followed by partial digestion with EcoRI. Chumakov, I. et al., *Journal of Virology*, 42:1088–1098 (1982). The fragment extending from the Xho I site at 2.0 U in MuLV, through the 3' LTR, 3' mouse flanking sequence, all of pBR322, and ending at the EcoRI site was purified from an agarose gel after electrophoretic separation. Vogelstein, B. and D. Gillespie, *Proceedings of the National Academy of Sciences*, USA, 761:615–619 (1979). The second fragment was obtained by digestion of pMOV Psi+ with Bal I to completion followed by purification of the fragment extending from the Bal I site in pBR322 through 5' mouse flanking sequence and 5' LTR to the Bal I site located at 0. 7 U of MuLV. HindIII linkers (Collaborative Research) were then blunt-ligated to this fragment with T4 DNA ligase, and the fragment was digested with excess HindIII and EcoRI. The LTR-containing fragment was purified from an agarose gel after electrphoretic separation. The third fragment present in the final ligation reaction was obtained from pSV2gag/pol where the gag/pol region of MuLV had been subcloned into pSV2. Mulligan, R. C. and P. Berg, *Science*, 209:1422–1427 (1980). pSV2- gag/pol was digested to completion with Xho I and HindIII and the fragment extending from the HindIII site (changed from the Pst I site at 1.0 U of MuLV) to the Xho I site at 2.0 of MuLV was purified from an agarose gel following electrophoretic separation. These three DNA fragments were then mixed in equimolar amounts at a total DNA concentration of 50 ug/ml. in ligase buffer (50 mM Tris-HCl [pH 7.8], 10 mM $MgCl_2$, 20 mM dithiothreitol, 1.0 mM ATP, 50 ug/ml. bovine serum albumin) and incubated with T4 DNA ligase for 18 hr. at 15 C. *E. coli* HB101 was transfected with the ligated DNA, and ampicillin resistant transfectants were obtained. The plasmid DNA obtained from a number of transformants was screened for the desired structure by digestion with appropriate restriction endonucleases and electrophoresis through agarose gels. Davis, R. W. et al., *Methods in Enzymology*, 65:404–411 (1980).

Cell lines containing the Psi mutant stably integrated into the chromosome were made by cotransfection of pMOV-Psi and pSV2gpt, a SV40 hybrid vector capable of XG PRT expression. Mulligan, R. C. and P. Berg, *Science*, 209:1422–1427 (1980). Cells from gpt+ colonies obtained in this way were cloned and established into three lines: Psi-1, Psi-2, and Psi-3.

The Psi 2 cell line described by Mulligan and co-workers was created by transfecting NIH 3T3 endothelial cells with pMOV-Psi, which is an ecotropic Moloney murine leukemia virus (Mo-MuLV) clone. pMOVPsi expresses all the viral gene products but lacks the Psi sequence, which is necessary for encapsidation of the viral genome. pMOV-Psi- expresses an ecotropic viral envelope glycoprotein which recognizes a receptor present only on mouse (and closely related rodent) cells.

Another cell line is the Psi am line, which are Psi-2-like packaging cell lines. These Psi-am cell lines contain a modified pMOV-Psi-genome, in which the ecotropic envelope glycoprotein has been replaced with envelope sequences derived from the amphotropic virus 4070A. Hartley, J. W. and W. P. Rowe, *Journal of Virology*, 19: 19–25 (1976). As a result, they are useful for production of recombinant virus with amphotropic host range. The retrovirus used to make the Psi am cell line has a very broad mammalian host range (an amphotropic host range) and can be used to infect human cells. If the recombinant genome has the Psi packaging sequence, the Psi-am cell line is capable of packaging recombinant retroviral genomes into infectious retroviral particles. Cone, R. and Mulligan, R. C. *Proceedings of the National Academy of Sciences, USA*, 81:6349–6353 (1984).

Two other packaging cell lines are known as Psi CRIP and Psi CRE. These cell lines have been shown to be useful to isolate clones that stably produce high titers of recombinant retroviruses with amphotropic and ecotropic host ranges, respectively. These cell lines are described in Danos, O. and R. C. Mulligan, *Proceedings of the National Academy of Sciences, USA*, 85: 6460–6464 (1988) and in U.S. patent application Ser. No. 07/239,545 filed Sep. 1, 1988. The teachings of the reference and the patent application are incorporated herein by reference. Psi CRIP and Psi CRE have been deposited at the American Type Culture Collection, Rockville, Md., under accession numbers CRL 9808 and CRL 9807, respectively, under the terms of the Budapest Treaty.

The wild type retroviral genome has been modified by Cone and Mulligan for use as a vector capable of introducing new genes into cells. As shown in FIGS. 2, the gag , the pol and the env genes have all been removed and a DNA segment encoding the neo gene has been inserted in their place. The neo gene serves as a dominant selectable marker. The retroviral sequence which remains part of the recombinant genome includes the LTRs, the tRNA binding site and the Psi packaging site. Cepko, C. et al., *Cell*, 37:1053–1062 (1984).

Additional vector constructions which have been used in producing transduced endothelial cells of the present invention are represented in FIG. 2 and are described in detail below.

pLJ. The characteristics of this vector have been described in Korman, A. J. et al., *Proceedings of the National Academy of Sciences. USA*. 84:2150 (1987) . This vector is capable of expressing two genes: the gene of interest and a dominant selectable marker, such as the neo gene. The gene of interest is cloned in direct orientation into a BamHI/SmaI/SalI cloning site just distal to the 5' LTR, while, the neo gene is placed distal to an internal promoter (from SV40) which is farther 3' than is the cloning site (is located 3' of the cloning site). Transcription from PLJ is initiated at two sites: 1) the 5' LTR, which is responsible for expression of the gene of interest and 2) the internal SV40 promoter, which is responsible for expression of the neo gene. The structure of pLJ is represented in FIG. 2a.

Figure 2A:
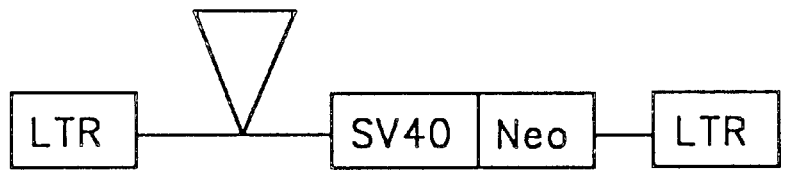
FIGS. 2A–2C show a schematic representation of retroviral vectors, each having a recombinant genome, useful in the present invention.
Figure 2B:
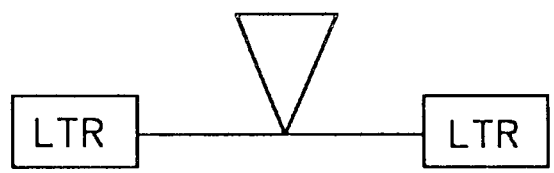

Vector pLJ is represented in FIG. 2a. In pLJ, the genetic material of interest is inserted just following the 5' LTR. Expression of this genetic material is transcribed from the LTR and expression of the neo gene is transcribed from an internal SV40 promoter.

pEm. In this simple vector, the entire coding sequence for gag, pol and env of the wild type virus is replaced with the gene of interest, which is the only gene expressed. The components of the pEm vector are described below. The 5' flanking sequence, 5' LTR and 400 bp of contiguous sequence (up to the BamHI site) is from pZIP. The 3' flanking sequence and LTR are also from pZIP; however, the ClaI site 150 bp upstream from the 3' LTR has been ligated with synthetic BamHI linkers and forms the other half of the BamHI cloning site present in the vector. The HindIII/EcoR1 fragment of pBR322 forms the plasmid backbone. This vector is derived from sequences cloned from a strain of Moloney Murine Leukemia virus. An analogous vector has been constructed from sequences derived from the myeloproliferative sarcoma virus. The structure of pEm is represented in FIG. 2b.

Vectors without a selectable marker can also be used to transduce endothelial cells with genetic material of interest. Such vectors are basically simplifications of the vectors previously described, in which there is such a marker. Vector pEm is represented in FIG. 2b; as represented, the main components of the vector are the 5' and 3' LTR, and the genetic material of interest, inserted between the two LTRs.

MFG

Figure 2C:
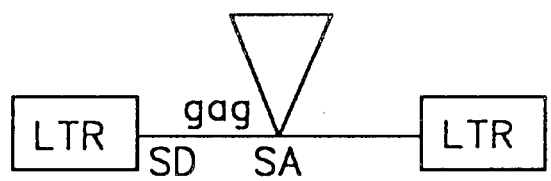

The MFG vector (ATCC accession no. 68754) is similar to the pEm vector but contains 1038 base pairs of the gag sequence from MMLV to increase the encapsulation of recombinant genomes in the packaging cell lines, and 350 base pairs derived from MOV-9 which contains the splice acceptor sequence and transcriptional start. An 18 base pair oligonucleotide containing NcoI and BamHI sites directly follows the MOV-9 sequence and allows for the convenient insertion of genes with compatible sites. The MMLV LTR controls transcription and the resulting mRNA contains the authentic 5' untranslated region of the native gag transcript followed directly by the open reading frame of the inserted gene. The structure of MFG is represented in FIG. 2c. A more detailed map of MFG is provided in FIG. 19.

MFG was constructed by ligating the 5' LTR containing XhoI/NdeI fragment of the half-GAG retroviral vector ( half-GAG is described in Bender, et al., J. Virol. 6I:1639–1646) to an XhoI/BamHI H4 histone promoter fragment. Retroviral vector pEMB was digested with NdeI and BamHI, and the 3' LTR containing fragment was ligated to the half GAG fragment already ligated to the H4 fragment so as to produce an intermediate retrovirus vector containing 2 LTRs in the proper orientation and also containing the H4 fragment within the viral portion of the vector. The intermediate vector was then linearized by digestion with NdeI and the NdeI site in the pB322 portion of the vector was filled in by polymerase and destroyed by ligation. The vector was subsequently digested with XhoI and the XhoI site was joined to an NdeI linker. The vector was subsequently cleaved with BamHI and the large fragment containing both LTRs and the pBR322 sequence) was purified.

Figure 19:
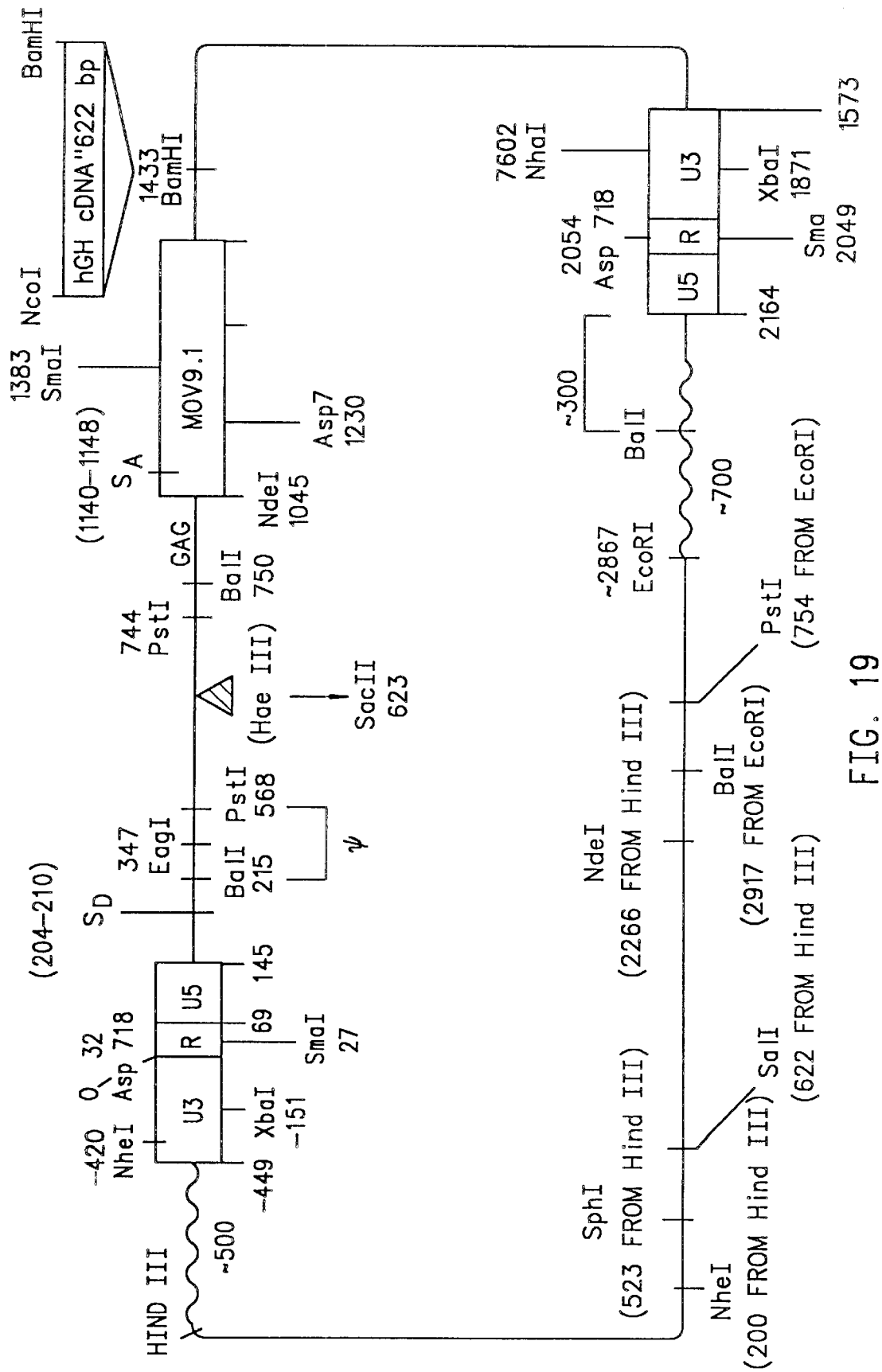
FIG. 19 is a map of the retroviral vector MFG.

A linker having XhoI and BamHI and having the following sequence:

CTAGACTGCCATGGCGCG TGACGGTACCGCGCCTAG was synthesized and ligated to both the BamHI site on the cleared intermediate vector and an NdeI/XbaI fragment from pMOV9 [containing a splice acceptor site next to the NdeI edge] so as to form a circular vector, MFG as illustrated in FIGS. 2c and 19.

αSGC

Figure 2D:
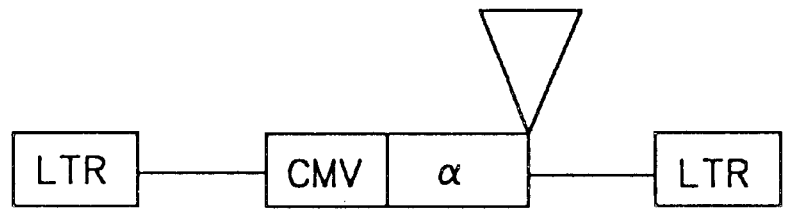

The aSGC vector (ATCC accession number 68755) utilizes transcriptional promoter sequences from the α-globin gene to regulate expression of the tPA gene. The 600 base pair fragment containing the promoter element additionally contains the sequences for the transcriptional initiation and 5' untranslated region of the authentic α-globin mRNA. A 360 base pair fragment which includes the transcriptional enhancer from cytomeglovirus precedes the α-globin promoter and is used to enhance transcription from this element. Additionally, the MMLV enhancer is deleted from the 3' LTR. This deletion is transferred to the 5' LTR upon infection and essentially inactivates the transcriptional activating activity of the element. The structure of α-SGC is represented in FIG. 2d. A more detailed description of α-SGC is provided in FIG. 18.

Introduction of Genetic Material into Endothelial Cells and Assessment of Expression of the Genetic Material The recombinant amphotropic retrovirus produced by the packaging cell line is used to infect endothelial cells. As described above, the recombinant genome of the amphotropic retrovirus can include a variety of components, but in general is comprised of two LTRs and, in place of the gag, the pol and the env sequences, a second promoter sequence. In some cases, it also includes a gene encoding a selectable marker (e.g., neo).

Viral stocks, to be used in introducing genetic material of interest into endothelial cells, are harvested, as described above, supplemented with 8 micrograms per mil. (mcg/ml.) of polybrene (Aldrich) and added to the culture of endothelial cells. If the titer of the virus is high (e.g., approximately $10^6$ Cfu per ml. ) , then virtually all endothelial cells will be infected and no selection (e.g., of endothelial cells into which the vector, including the recombinant genome, has been introduced) is required. If the titer is very low, then it is necessary to use a retroviral vector that has a selectable marker, such as neo. If a selectable marker is used, after exposure to the virus, the cells are grown to confluence and split into selective media (e.g., media containing the antiobiotic, G418).

The neo gene is a bacterial gene derived from the transposon Tn5, which encodes neomycin resistance in bacteria and resistance to the antibiotic G418 in mammalian cells. This neo gene acts as a dominant selectable marker; its presence in a mammalian cell converts the cell into one which will grow in the presence of G418, an antibiotic which generally causes cell death. As a result, the presence of this gene in a mammalian cell can be determined by culturing cells in media which contains G418. The recombinant retrovirus having this recombinant genome is referred to as the neo virus.

The recombinant retroviral vectors having the neo gene also have a cloning site. As a result, genetic material of interest can be introduced into the vector, incorporated into endothelial cells along with the neo gene and expressed by endothelial cells transduced with the recombinant retrovirus (referred to as endothelial cells having incorporated genetic material).

It should be possible to express virtually any gene of interest in endothelial cells by means of a retroviral vector. Retroviral vectors that express genes that encode three different classes of proteins have been constructed: a secreted hormone or polypeptide (e.g., hPTH, tPA or factor VIII), a membrane receptor (receptor for LDL, LDLR), and an intracellular enzyme (beta-galactosidase). Efficient expression of the recombinant retroviral vector when incorporated into endothelial cells has been demonstrated and is described in detail in the examples.

Introduction of Genetic Material Encoding Other Proteins or Polypeptides

Genes encoding other proteins or polypeptides can also be introduced into endothelial cells by means of an appropriate retroviral vector. For example, a gene encoding human growth hormone (hGH), a gene encoding clotting Factor IX or a gene encoding insulin can be introduced into endothelial cells. Such genes can be introduced into endothelial cells, alone or in combination with a gene encoding a selectable marker, such as the neo gene.

These genes, as well as others can be introduced into endothelial cells in the same manner as described above for the hPTH gene and the resulting transduced endothelial cells can be implanted into or applied onto an appropriate site in the body.

Other Vehicles and Means for the Introduction of Genetic Material of Interest into Endothelial Cells It is also possible to use vehicles other than retroviruses to genetically engineer or modify endothelial cells. Genetic information of interest can be introduced into endothelial cells by means of any virus which can express the genetic material of interest in such cells. For example, SV40, herpes virus, adenovirus and human papilloma virus can be used for this purpose.

It is also possible to introduce genetic material of interest into endothelial cells in such a manner that it is not incorporated stably into the recipient cells, but is expressed episomally (remains distinct or separate from the recipient cell genome).

In addition chemical or physical means can be used to introduce genetic material of interest into endothelial cells. An example of a chemical means is the commonly used calcium phosphate transfection procedure and an example of a physical means is electroporation whereby cells are exposed to an electric current which enables the entry into the cell of genetic material of interest.

Uses of Endothelial Cells Having Incorporated Genetic Material

Improvement of Performance of Vascular Grafts or Implants

Many important disease states involve stenosis or occlusion of arteries that supply vital organs. The pathologic mechanism most commonly implicated in such disease states is atherosclerosis. Examples include angina pectoris and myocardial infarction due to coronary artery disease; transient ischemic attacks and strokes due to cerebral vascular disease; renal vascular hypertension, and ultimately, renal failure due to renal artery stenosis; and claudication of the lower extremities, which is caused by vascular disease of peripheral arteries and, in its most severe form, can result in amputation. Unless the agents that predispose an individual to atherosclerotic lesions are eliminated (e.g., hypertension, cigarette smoking) the natural history of these disease states is usually progression of the atherosclerotic lesions, resulting in permanent damage or death.

An accepted and widely used therapeutic approach to advanced atherosclerotic disease is to bypass the site of major stenosis of occlusion with a prosthetic vessel made of synthetic material, such as Dacron or Gortex. More than 350,000 vascular grafts are implanted each year. One major problem with this approach is that the prosthetic vessel is extremely thrombogenic (i.e., it has the propensity to develop clots), which leads to a very high rate of restenosis. It has been possible to reduce this problem by seeding the lumen of the prosthetic vessels with autologous endothelial cells; grafts lined with endothelial cells are presumably less thrombogenic. It is in this setting that modified endothelial cells would be particularly useful.

Endothelial cells can be genetically modified according to the method of the present invention to improve their performance in the context of an endothelial cell-lined prosthetic implant. Existing protocols for using endothelial cell-lined prosthetic implants are complicated by several significant technological problems, most of which can be overcome through the use of genetically engineered endothelial cells.

A problem with endothelialized implants is that the lumen of the prosthetic vessel undergoes progressive narrowing due to the proliferation of smooth muscle cells between the wall of the prosthesis and the luminal surface. One way in which this can be prevented is to introduce into the endothelial cells a gene that secretes a product which inhibits the growth of smooth muscle cells. Many types of autocrine:paracrine growth factors that control proliferation of mesenchymal and/or epithelial cells have recently been identified and their genes cloned. Such genes can be introduced into endothelial cells using the method of the present invention. The resulting transduced endothelial cells produce the cell growth inhibitor.

A further technical problem of endothelialized implant protocols is that the binding (plating) efficiency of the endothelial cells to the prosthetic graft is relatively low. Previous attempts to improve this have been directed at modifying the composition of the graft surface and have been of limited success. Using the method of the present invention, it is possible to introduce into endothelial cells a gene which encodes a membrane receptor. The lumen of the prosthetic vessel can then be coated with the ligand for the receptor, thereby facilitating binding of endothelial cells to the luminal surface through the membrane receptor/ligand interaction.

Genetically engineered endothelial cells of the present invention can be used to decrease the thrombogenicity of endothelial cell-lined prosthetic grafts. The mechanism of clot formation is believed to be platelet adhesion followed by deposition of fibrin and propagation of clot. This could be minimized or possibly eliminated by seeding the grafts with genetically engineered endothelial cells that secrete a thrombolytic agent (e.g., an agent which dissolves clots, such as tissue plasminogen activator (TPA) or streptokinase).

Use of Modified Endothelial Cells to Deliver a Product to a Limb or Organ

This invention can also be used to introduce into endothelial cells genes that secrete factors which would be beneficial to the limb or organ perfused by the artery containing the prosthesis. For example, a common clinical problem is the presence of extensive narrowing of small vessels distal to the site of the prosthetic vessel. This is characteristic of the vascular disease associated with diabetes mellitus. Revascularization of the larger vessels with implants leads to incomplete reconstitution of perfusion to the affected limb or organ.

A way of promoting vascular flow to a compromised organ or limb is to maximally dilate all afferent vessels. Attempts to do this with oral or parenteral medicines have resulted in little therapeutic benefit, accompanied by many systemic side effects. This is caused, in part, by the fact that the vasodilator is not targeted to the appropriate tissue. Endothelial cells engineered to secrete a potent vasodilator such as atrial naturetic factor is an alternative approach. In this application, transduced endothelial cells proximate to the affected organ or limb can be implanted or generated by in vivo transduction thus resulting in the affected organ or limb being perfused with arterial blood containing a very high concentration of a vasodilator. This results in an increase in the overall vascular perfusion. However, the vasodilator is diluted to non-pharmacologic levels upon return to the heart, thereby obviating the many systemic side effects of vasodilators that occur when administered in a systemic nonselective manner.

Use of Modified Endothelial Cells as a Delivery System

The present invention makes it possible to genetically engineer endothelial cells in such a manner that they produce a selected protein or polypeptide, such as selected polypeptides and proteins not normally produced in endothelial cells in biologically significant amounts, and secrete them into the bloodstream or other area of the body (e.g., the central nervous system). The endothelial cells formed in this way can serve as a continuous drug delivery system to replace present regimens, which require periodic administration (by injection, infusion etc.) of the needed substance.

For example, it can be used to provide continuous delivery of insulin, which, at the present time, must be isolated from the pancreas, extensively purified and then injected into the body by those whose insulin production or utilization is impaired. In this way, insulin can be introduced into the body via a continuous drug delivery system and, as a result, there would be no need for daily injections of insulin.

Genetically engineered endothelial cells can also be used for the production of clotting factors. Hemophiliacs lack a protein called Factor VIII, which is involved in clotting. Factor VIII is now administered by injection. However, transduced endothelial cells having genes encoding Factor VIII can produce and deliver Factor VIII in viro.

Incorporation of genetic material of interest into endothelial cells can be particularly valuable in the treatment of inherited disease and the treatment of acquired disease. In the case of inherited diseases, this approach is used to provide genetically modified endothelial cells and other cells which can be used as a metabolic sink. That is, such endothelial cells would serve to degrade a potentially toxic substance that had accumulated to high levels in the patient. For example, transduced endothelial cells expressing the gene encoding adenosine deaminase can be used in treating an inherited form of severe combined immunodeficiency caused by a deficiency in the enzyme adenosine deaminase which results in the accumulation of toxic purine nucleosides. Endothelial cells of the present invention can also be used in the treatment of genetic diseases in which a product (e.g., an enzyme or hormone) normally produced by the body is not produced or is made in insufficient quantities. Here, endothelial cells transduced with a gene encoding the missing or inadequately produced substance can be used to produce it in sufficient quantities. For example, this can be used in producing alpha-1 anitrypsin the missing protein or defective protein in an inherited form of emphysema.

There are many acquired diseases for which treatment can be provided through use of genetically engineered endothelial cells (i.e., endothelial cells transduced with genetic material of interest). For example, such cells can be used in treating anemia, which is commonly present in chronic disease and often associated with chronic renal failure (e.g., in hemodialysis patients)

In this case, endothelial cells having incorporated in them a gene encoding erythropoietin would correct the anemia by secreting erthropoitin thus stimulating the bone marrow to increase erythropoiesis (i.e. production of red blood cells).

Transduced endothelial cells of the present invention can also be used to administer a low systemic dose of tissue plasminogen activator as an activator to prevent the formation of thrombi. In this case, endothelial cells having incorporated genetic material which encodes tPA would inhibit clotting in an individual in whom thrombus prevention is desired. This would be useful, for example, as a prophylactic against common disorders such as coronary artery disease, cerebrovascular disease, peripheral vascular occlusive disease, vein (e.g., superficial) thrombosis, such as seen in pulmonary emboli, or deep vein thrombosis. Endothelial cells which contain DNA encoding calcitonin can be used in the treatment of Paget's Disease, a progressive, chronic disorder of bone metabolism. Present treatment relies on subcutaneous administration of calcitonin.

Endothelial cells engineered to produce and secrete interleukins (e.g., IL-1, IL-2, IL-3) can be used in several contexts. For example, the result of some of the therapies now used (e.g., chemotherapy) is induction of neutropenia (the presence of abnormally low numbers of neutrophils in the blood), often caused by direct suppression of the bone marrow. For example, use of virtually all the chemotherapeutic agents, as well as AZT, used in the treatment of (AIDS) Acquired Immune Deficiency Syndrome, results in neutropenia. This condition results in numerous lifethreatening infections. In these cases, administration of, for example, IL-3 through implantation of endothelial cells which contain genetic material encoding IL-3 and thus express and secrete IL-3 can be used to increase the neutrophil count. In addition, the administration of thrombopoietin, which stimulates the production of platelets, can be used in the treatment of numerous conditions in which platelet count is low. In this case, endothelial cells transduced with the gene for thrombopoietin can stimulate platelet production.

Another related application of endothelial cells having incorporated genetic material is in the treatment of AIDS. Interleukin 2 and Interleukin 3, which stimulate the immune system, are potentially valuable in the treatment of AIDS. These molecules could be delivered by endothelial cells which have been genetically engineered to produce these two polypeptides (which are now administered by periodic injection).

Another use of the present invention is in the treatment of enzyme defect diseases. In this case the product encoded by the gene introduced into endothelial cells is not secreted (as are hormones); rather, it is an enzyme which remains inside the cell. There are numerous cases of genetic diseases in which an individual lacks a particular enzyme and is not able to metabolize various amino acids or other metabolites. The correct genes for these enzymes could be introduced via transduced endothelial cells. For example, there is a genetic disease in which those affected lack the enzyme adenosine deaminase. This enzyme is involved in the degradation of purines to uric acid. It might be possible, using the present invention, to produce transduced endothelial cells, which express the missing enzyme at sufficiently high levels to detoxify the blood as it passes through the area in which the transduced cells are present in the body.

The present invention also has veterinary applications. Transduced endothelial cells can be used, for example, in delivering substances such as drugs and hormones to animals, which would otherwise be provided by being injected periodically (e.g., daily or less frequently). Use of the modified endothelial cells of the present invention has the advantage that the presence of the modified cells within the animal and will provide quantities of the encoded protein on an ongoing basis, thus eliminating the need for daily/periodic administration of the substance.

The present invention will now be illustrated by the following examples, which are not intended to be limiting in any way.

EXAMPLE 1

Production of Human Parathyroid Hormone in Transduced Endothelial Cells

At the BamHI cloning site of pLJ, genetic material of interest can be inserted. The genetic material of interest can be DNA as described above.

Figure 3:
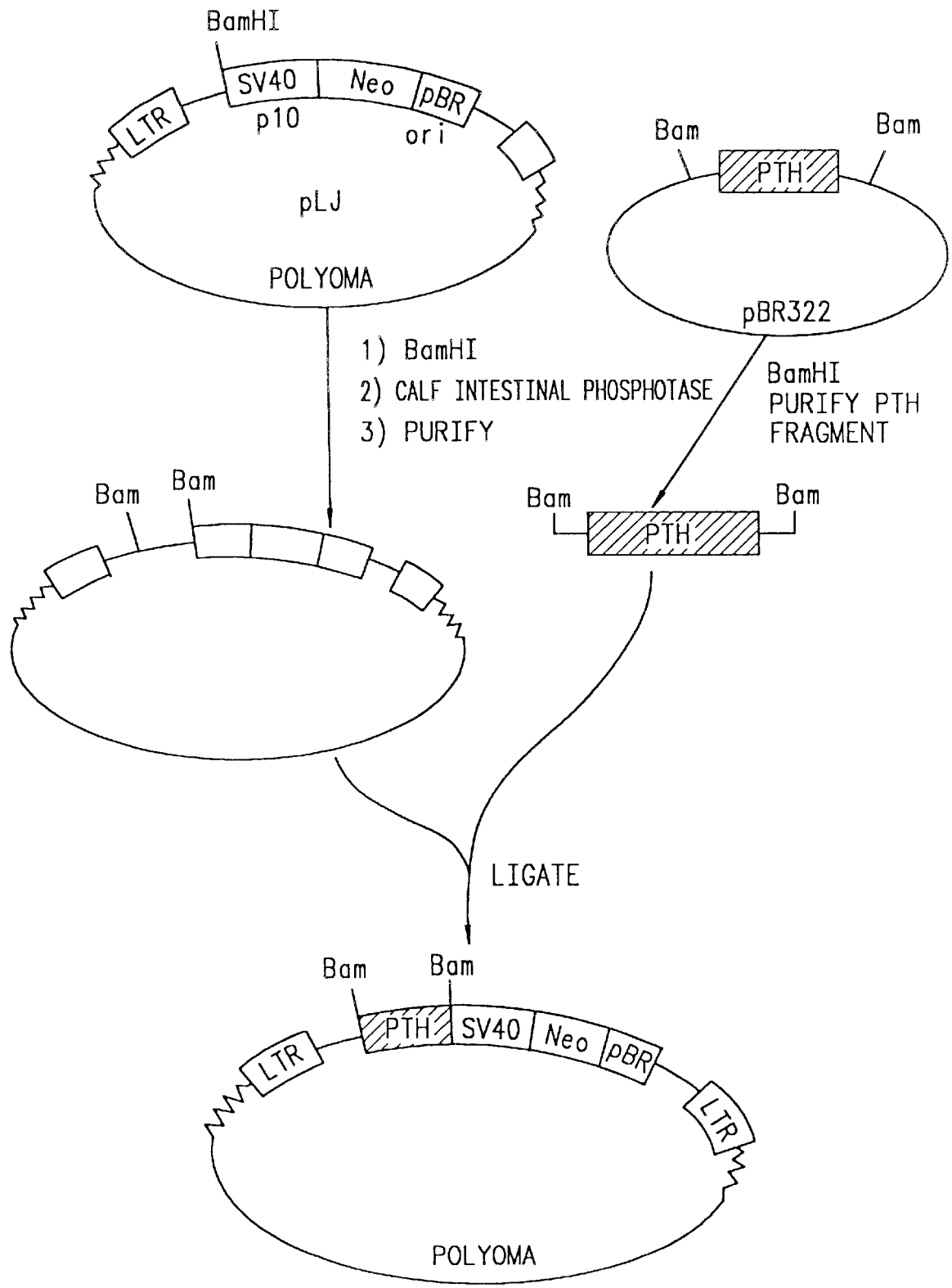
FIG. 3 is a schematic representation of the construction of a recombinant retroviral vector, using the pLJ vector represented in FIG. 2a and the human parathyroid hormone gene.
Figure 4A:
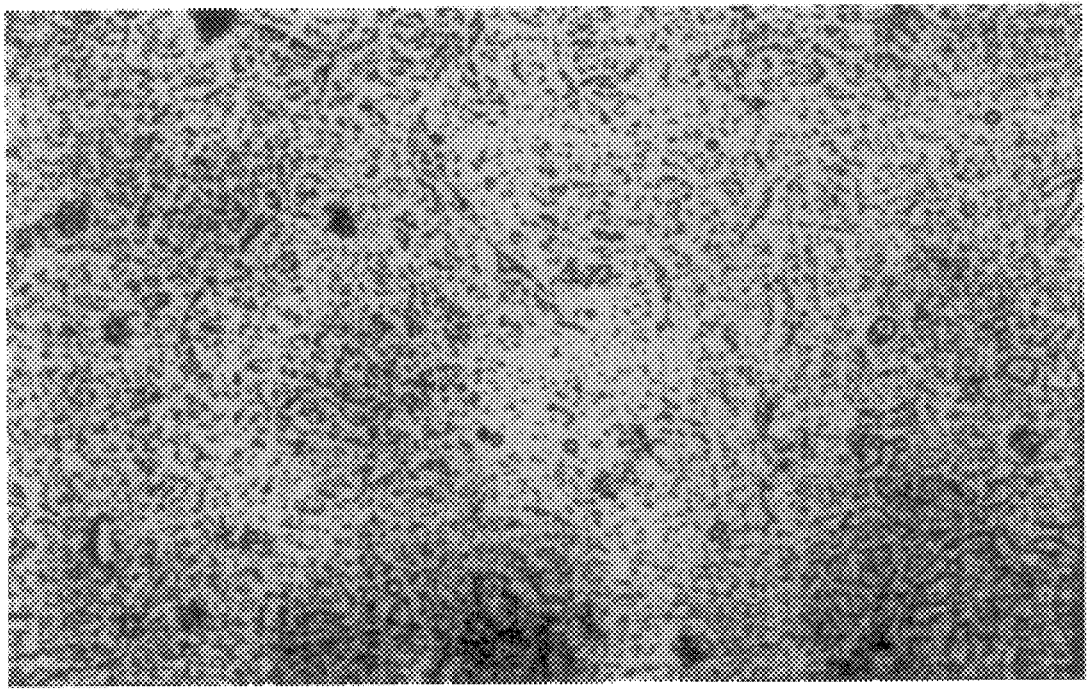
FIGS. 4A–4D include photographs of bovine aortic endothelial cells infected with a retrovirus that expresses low density lipoprotein receptor (LDLR) and analyzed for the uptake of fluorescent labeled LDL. Panel A—uninfected bovine aortic endothelial cells under phase contrast; Panel B—uninfected bovine aortic endothelial cells under fluorescent illumination; Panel C—infected bovine aortic endothelial cells under phase contrast; Panel D—infected bovine aortic endothelial cells under fluorescent illumination.
Figure 4B:
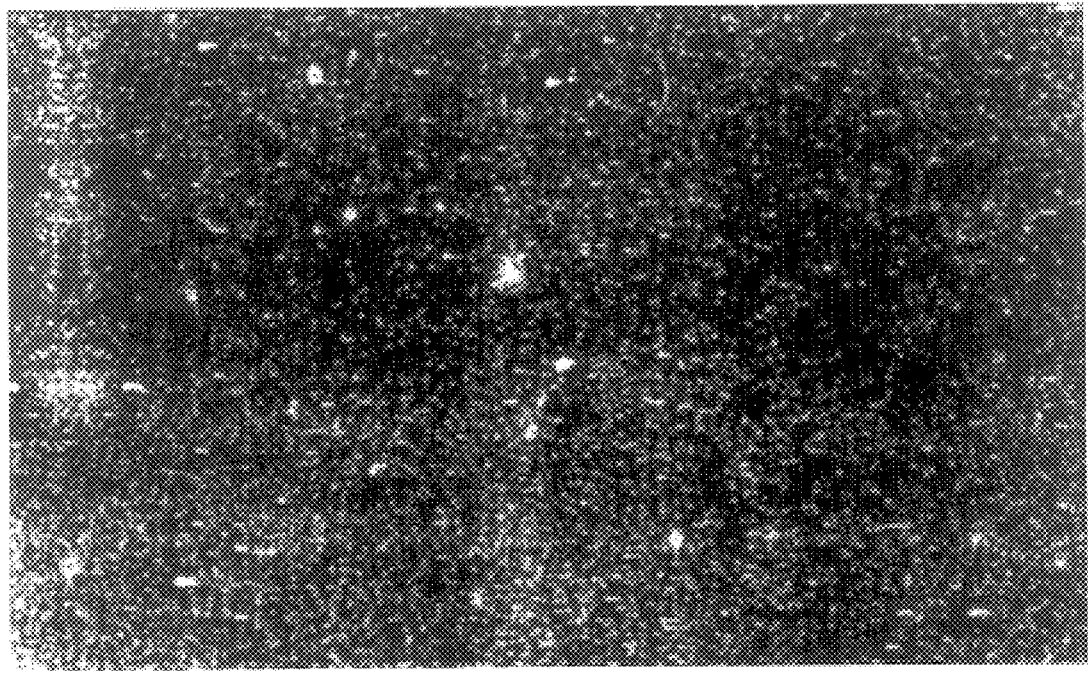
Figure 4C:
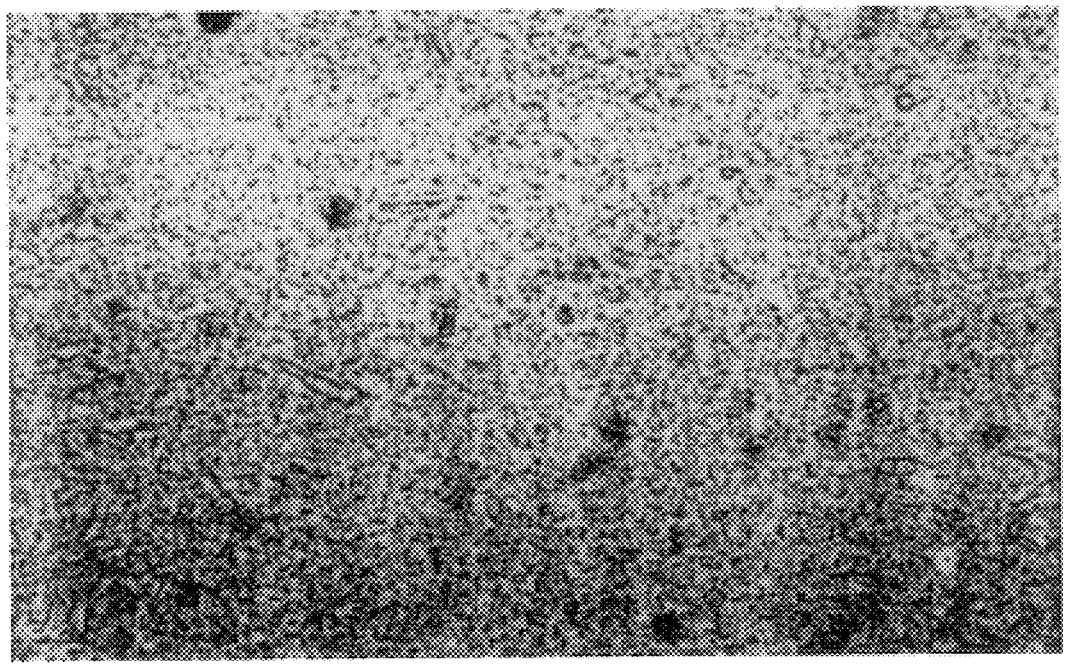
Figure 4D:
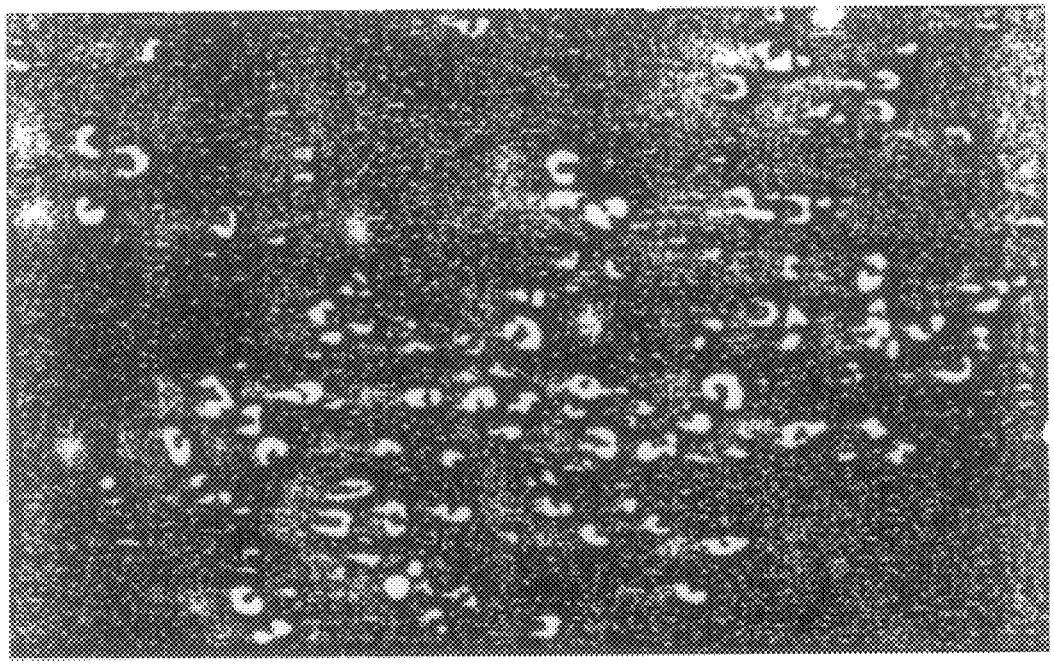

In particular, a copy of the gene encoding human parathyroid hormone (hPTH) has been cloned into this site, (e.g., into pLJ) in the following way: The pLJ plasmid was digested with BamHI and subsequently treated with the enzyme calf intestinal phosphatase. Following this, the linear vector was fractioned on agarose gel and purified, using glass beads. In addition, the BamHI fragment containing the human PTH gene was prepared from the plasmid described by Hendy et al., which contains a complete cDNA of human PTH cloned into pBR322. Hendy, G. N., et al., *Proc. Natl. Acad. Sci. USA*, 78:7365–7369 (1981). See FIG. 3.

A sub fragment of the PTH cDNA, containing 17 bp of 5' untranslated, all coding and 155 bp of 3' untranslated sequence, was isolated by digesting the initial plasmid with DdeI and HinfI and isolating the 600 bp fragment. The fragment was incubated with DNA polymerase in the presence of deoxynucleoside in phosphates, to fill in the recessed ends. BamHI linkers were ligated to the blunt ends with T4 DNA ligase. An authentic BamHI restriction fragment was generated by digesting this litigation mixture with BamHI. This was then subcloned into the BamHI site of pBR322, which is the plasmid used as the source of hPTH in vector construction.

Equal quantities of the pLJ linear backbone and the BamHI PTH fragment were added together, in the presence of T4 DNA ligase. The resulting mixture was maintained under conditions appropriate for ligation of the two fragments. The ligation mixture was used to transform bacterial HB101, which were then plated onto agar containing kanamycin. Maniatis, T. et al., *Molecular Cloning: A Laboratory Manual*, Cold Spring Harbor Laboratory, p.p. 250–251, 504; Bolivar, F. and K. Backman, In: *Methods in Enzymology*, R. Wu (ed.), Vol. 68, Academic Press, N.Y. (1979). The resulting colonies were analyzed for the recombinant plasmid.

Parathyroid hormone is a polypeptide which has a role in the regulation of calcium in the body. Although the hPTH gene is present in human endothelial cells, it is not expressed in those cells at biologically significant levels. Endothelial cells capable of making a polypeptide hormone such as hPTH, or another substance not normally made by such cells at biologically significant levels, can be engrafted onto or implanted into an individual and serve as a continuous synthesis and delivery system for the hormone, or other substance.

The Psi am cells producing the recombinant virus construct which contained the hPTH-encoding DNA and DNA encoding a selectable marker (such as the neo gene), were used to produce a viral stock, as described above. The viral stock was harvested; endothelial cells to be transduced with the virus containing the hPTH gene were incubated with the stock. In this case, a selectable marker is used to identify and select for transduced endothelial cells by culturing on media containing G418. If the viral titer is sufficiently high, essentially all endothelial cells are infected and selection, using a selectable marker and appropriate media, is not needed.

The ability of endothelial cells transduced with the recombinant retrovirus having the hPTH gene to express the hPTH gene has been assessed in vitro as follows: The bovine aortic endothelial cells were derived from an explant from the aorta of a calf. The cellshave a limited life span and are referred to as secondary cultures. Bovine aortic endothelial cells were infected with virus and not selected in neomycin, as described above. Transduced bovine aortic endothelial cells were seeded onto 10 cm tissue culture dishes and grown to confluence. Fresh culture media (DME with 10% CS and penicillin and streptomycin) was then added; this point is referred to subsequently as time zero. At the end of 24 hours, the media was removed and the cells were assayed for the production of human PTH.

The aliquots were analyzed for the presence of hPTH using a radioimmunoassay (Nichols) which measures intact hPTH. The technique is described in Allegro™ Intact PTH/Immunoassay System for the Quantitative Determination of Human Intact Parathyroid Hormone in Serum, Nichols Institute Diagnostics, San Juan Capistrano, Calif. (36B-2170, Effective 7/86 Revised), the teachings of which are incorporated herein by reference. The assay has a sensitivity of approximately one nanogram/milliliter serum (ng/ml) and was shown to be specific for human PTH in that it does not cross react with calf PTH. The results of the experiments are reported as the production of hPTH, as measured by RIA, over time. Results are shown in Table I.

TABLE I

Production of hPTH in Transduced BAE Cells

| Cell PTH Production | |
|---|---|
| Control BAE* | <10 pg/106/24h |
| Transduced BAE | 6.3 ng/106/24h |

*BAE = bovine aortic endothelial

Endothelial cells from a bovine aorta transduced with DNA encoding hPTH according to the method of the present invention have been deposited at the American Type Culture Collection (Rockville, Md.) under deposit number CRL9601.

EXAMPLE 2

Production of Human LDL Receptor in Transduced Endothelial Cells

The cDNA for human LDL receptor (LDLR) was inserted into the pEm vector. The cDNA for LDLR was prepared for insertion into the pEM as follows. LDLR cDNA was excised from the vector pTZ1 (obtained from Dr. Goldstein, University of Texas Health Science Center) by digestion with HindIII. The 2.6 kb HindIII fragment containing all of the LDLR coding sequence was blunt ended with Klenow fragment and BclI oligonucleotide linkers (from NEB) were ligated to the cDNA with T4 DNA ligase. Finally, this ligation mixture was digested with an excess of the enzyme BclI and the fragment was fractionated on an agarose gel and purified. This was inserted into the BamHI cloning site of pEm as follows. pEm was digested with BamHI and the linearized plasmid was digested with calf intestinal phosphatase. Equal quantities of the linkered LDLR insert and pEm backbone were mixed and ligated with T4 DNA ligase. The ligation mixture was used to transform HB101 and ampicillin resistant colonies were analyzed for the appropriate retroviral vector. The pEm-LDLR vector was transfected into the Psi-am cell line and clones that produced high quantity of recombinant virus were identified. Viral stocks were used to infect cultures of bovine aortic endothelial cells as described for PTH.

In vitro assessment of LDLR expression was carried out as follows: confluent plates of control or transduced bovine aortic endothelial cells were incubated with LDL that had been conjugated with a fluorescent label (obtained from Biomedical Tech Inc., Stoughton, Mass.) at a concentration of 10 ug/ml for approximately 8 hours. Following this, the cells were washed with PBS and fixed in 0.5% gluteraldehyde in PBS. They were then visualized under a fluorescent microscope for the uptake of fluorescent labeled LDL (*LDL). The results of this experiment are presented in FIG. 4. Briefly, the level of endogenous LDLR is low, as evidenced by the relative lack of *LDL uptake in uninfected cultures (See 4B). However, in cultures infected with the LDLR virus, approximately 30% of all cells take up detectable quantities of *LDL, thereby documenting efficient expression of the exogenous LDLR (See 4D).

EXAMPLE 3

Production of Beta-galactosidase in Transduced Endothelial Cells

Figure 5A:
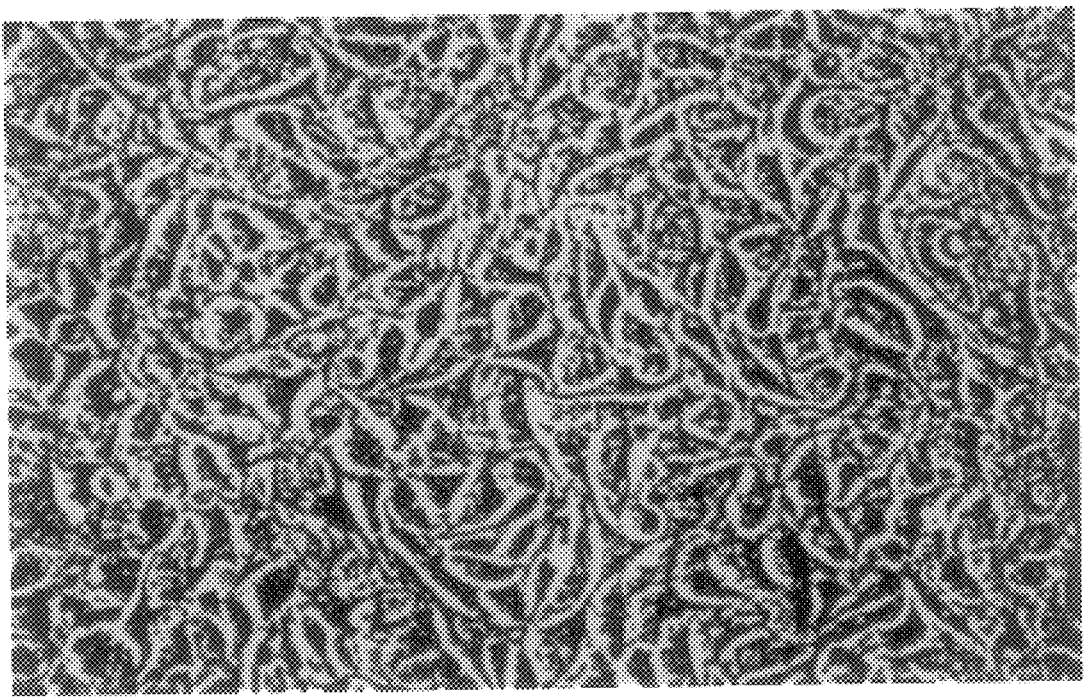
FIGS. 5A–5B include photographs of bovine aortic endothelial cells infected with a retrovirus that expresses beta-galactosidase and analyzed for its expression using an in situ histochemical stain. Panel A—uninfected bovine aortic endothelial cells stained for beta-galactosidase activity; Panel B infected unselected bovine aortic endothelial cells stained for beta-galactosidase activity.
Figure 5B:
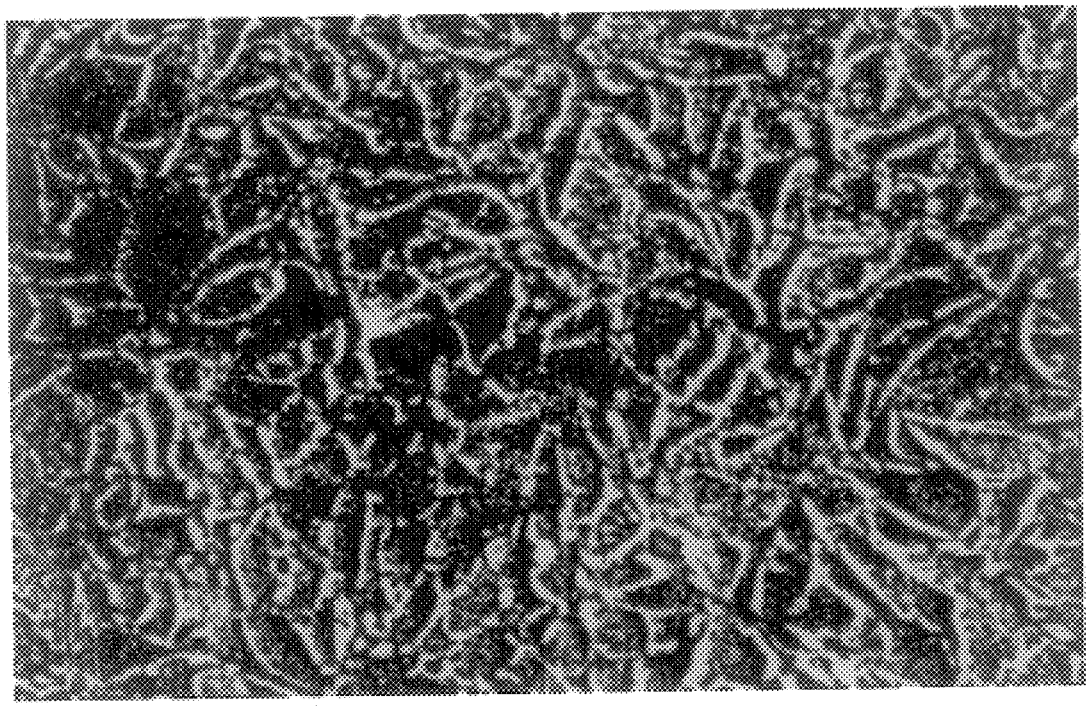

The gene endocing beta-galactosidase from *E. coli* was inserted into pLJ and this vector was transfected into the Psi-am cell line, resulting in production of high titer retroviral stocks. The construction of this vector and isolation of the producer cell line has been described by Price and coworkers. Price, J. et al., *Proceedings of the National Academy of Sciences, USA*, 84: 156–160 (1987). Stocks of virus encoding the beta-galatosidase gene were used to infect bovine aortic endothelial cells, as described earlier. The infected cultures were analyzed for beta-galatosidase expression using an in situ histochemical stain. See Price et al, above. Cultures were analyzed before and after selection in G418. The retroviral vector used in this experiment expresses both beta-galactosidase and the neo gene which confers resistance to G418. The histochemical stain was performed as described by Price et al. Briefly, cell cultures were fixed in 0.5% gluteraldehyde in PBS for 5 minutes, washed with PBS and exposed to the reaction mixture for at least 12 hours. The reaction mixture contains a substrate for beta-galatosidase which, when hydrolyzed, turns blue and precipitates in the cell. As a result, any cell expressing the viral encoded beta-galactosidase will turn blue. The results of this experiment are presented in FIG. 5. No beta-galactosidase activity is detected in cultures that were not exposed to virus (FIG. 5A); infected cultures demonstrate beta-galactosidase activity in about 30% of the cells (FIG. 5B). These transduced cells are selected for by incubating them in the presence of G418.

EXAMPLE 4

Figure 6:
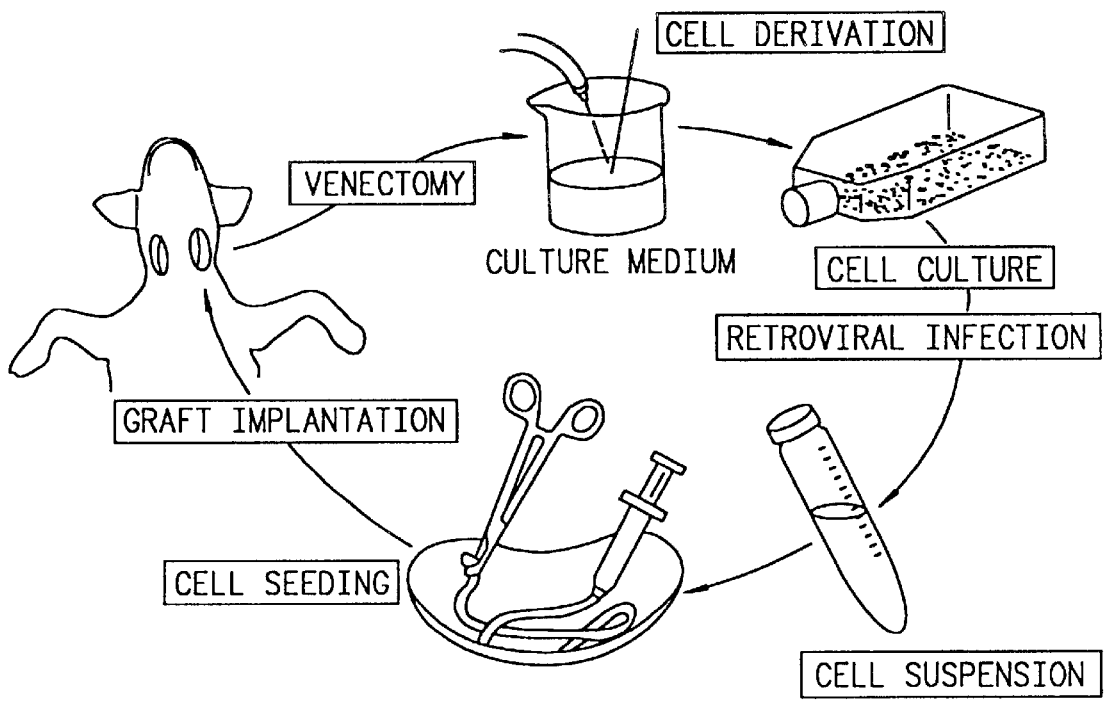
FIG. 6 is a pictorial representation depicting the transplantation of genetically modified endothelial cells into dogs.

Production of Beta-galactosidase in Transduced Endothelial Cells on the surface of Vascular Grafts Transplanted In Vivo A pictorial representation of a typical protocol for transduction and transplantation of endothelial cells is shown in FIG. 6. Endothelial cells were enzymatically harvested from external jugular veins of adult mongrel dogs which weighed 20–25 kg. Cells from each animal were divided into 2 aliquots; one to be infected with a replication defective retrovirus (see below) and the other to be mock infected. The enzymatically harvested cells were used to establish primary cultures. Endothelial cells were plated on to fibronectin coated flasks and maintained in M199 Medium supplemented with 5% plasma derived equine serum, penicillin, streptomycin, heparin and ECGF during two serial passages over a 10–14 day period.

During this time period, cells were exposed to fresh stocks of virus supplemented with polybrene (8 ug/ml) every 3 days (18 hr/exposure). At the end of the second passage, cells were harvested and aliquots were analyzed directly, cryopreserved, or used to seed 6 cm×4 mm knitted dacron TM drafts (CR BARD, Billerica, Mass.) according to a modification of the 4-step method of Yates ($0.75 \times 10^6$ cells were added to the autologous blood during the second and third step). Animals were anesthetized and 6 cm segments of both carotid arteries were replaced with the seeded grafts as described. Each animal received an implant seeded with infected endothelial cells and a contralateral graft seeded with mock infected cells. Five weeks after implantation, the animals were anesthetized and the grafts were harvested and analyzed.

Replication-defective retroviruses with amphotropic host range were used to stably introduce a reporter gene into the genomic DNA of the endothelial cells. The lacZ gene was used as the reporter gene because its product of expression, beta-galactosidase, can be detected in situ through the use of enzyme histochemical assays that stain the cell's cytoplasm blue. (Example 3). Efficiency of retroviral infection was estimated by Southern analysis which detects proviral sequences and by the cytochemical stain for viral-expressed beta-galactosidase which detects infected cells in situ.

There were two recombinant retroviruses used in these studies. The BAG vector has been described previously by Price et al., *Proceedings of the National Academy of Science, USA*, 84: 156–160 (1987). The BAG virus, containing the Lac Z-gene, expresses beta-galactosidase from the 5' LTR (Long Terminal Repeat) and a selectable marker (neo) from an SV40 derived promoter which confers resistance to kanamycin in prokaryotes and G418 in eukaryotes. Approximately 5–15% of the endothelial cells exposed to the BAG virus were infected; cultivation of these cultures in media supplemented with the aminoglycoside G418 effectively selected for transduced cells.

The BAL vector derived from the previously described BA-LDLR vector except LDLR cDNA sequences were replaced with the coding sequences for the *E. coli* beta-galactosidase gene. The higher titer BAL virus, containing the Lac Z-gene, expresses betagalactosidase from a promoter derived from the chicken beta-actin. Approximately 50% of the cells exposed to the BAL virus were transduced as measured by Southern analysis and by the in situ cytochemical stain for beta-galactosidase.

In Southern analysis, high molecular weight DNA was isolated and an aliquot (10 ug) was digested with Kpn I, fractionated on a 1% agarose gel, transferred to Zetabind and probed with a 1200 bp ClaI/EcoRI fragment that had been labeled to a high specific activity according to the method of Feinberg and Volt. Cytochemical characterization of cultured endothelial cells was demonstrated by both phase contrast and fluorescent micrographs. Retrovirus-infected endothelial cells were analyzed at the time of seeding and after removal from the implanted graft for uptake of DIL-AC-LDL and for expression of viral-directed beta-galactosidase. Preseeded and post-implantation cells that had been inoculated with DIL-AC-LDL were assessed using phase contrast and fluorescent micrographs. Preseeded and post-implanted cells were also analyzed for the expression of viral directed beta-galactosidase.

At the time of seeding, the cultures were analyzed for endothelial cell specific function (i.e., uptake of acetylated LDL, and the presence of Von Willebrands factor) and for the presence of antigens specific for smooth muscle cells. These analysis indicated that more than 98% of the cells from each isolate were functioning endothelial cells.

The experimental system was a modification of a previously described dog model that has been used to study graft repopulation. Dogs 1–3 received implants that had been seeded with BAG-infected, unselected endothelial cells while dogs 4-7 initially received implants seeded with BAL-infected, unselected endothelial cells. While these experiments were in progress, endothelial cells from dogs 4–7 were also infected with the BAG virus and expanded in culture in the presence or absence of G418, an aminoglycoside that selects for BAG-transduced cells. After 5 weeks, the grafts were explanted for analysis and new grafts were implanted in dogs 4–7 (referred to as dogs 4' 7'). Each of these dogs received a graft seeded with endothelial cells that were infected with BAG virus and selected in G418 and a contralateral graft seeded with BAG-infected unselected endothelial cells. The second set of grafts were again explanted after 5 weeks.

Analysis of the explanted grafts revealed that 18 of 22 remained patent after 5 weeks. Scanning electron microscopy demonstrated a lining of cells with endothelial-like morphology on the luminal surface of 14 of 18 patent grafts. When present, the endothelial cell lining was incomplete (50–90% of the total surface) and patchy in distribution with a paucity of cells seen along the peaks of the crimped dacron graft. A portion of each graft was fixed, stained for cells that express viral-derived betagalactosidase and visualized through a high power dissecting microscope with a magnification of 750X. Each graft seeded with infected endothelial cells that remained patent and retained luminal cells did contain beta-galactosidase-positive cells on the lumen of the vessel. Contralateral grafts seeded with MOCK infected endothelial cells never demonstrate positive staining cells.

In situ analysis of the grafts was performed for viral-transduced cells. Longitudinal sections of the genetically engineered implants were analyzed for cells that express viral-expressed beta-galactosidase. Grafts were cut longitudinally and a portion fixed in 0.5% gluteraldehyde for 5 minutes, washed in PBS three times, and incubated in x-gal solution for 2 hours and the luminal surface photographed with a Leitz dissecting microscope. The grafts were visualized enface and several interesting aspects of the seeding pattern were observed. The density of transduced cells was greatest in the deeper surfaces of the crimped graft. This was visualized under low power as rings of blue staining cells that line the crevices of the serrated surface and correlates with the variation in surface endothelial cell repopulation visualized by scanning electron microscopy. In addition there was no regional variation in the density or pattern of transduced cells with respect to proximity to the distal or proximal anastomosis. Finally, in each case the proportion of luminal cells which were positive for beta-galactosidase seemed qualitatively lower than the preparation of beta-galactosidase positive cells that were seeded.

Cells were enzymatically harvested from the luminal surface of portions of the grafts to permit a more detailed characterization. Primary cultures of cells were established and expanded in vitro for approximately 2–3 weeks prior to analysis. Genetically modified endothelial cells were identified in this population of cells by Southern analysis and by the cytochemical assay for viral-expressed beta-galactosidase. The majority of cells harvested from the graft and expanded in vitro retained differentiated endothelial function (less than 95%). However, the proportion of cells that expressed viral directed beta-galactosidase or contained proviral sequences was consistently diminished when compared to the cultures analyzed at the time of seeding. This disparity is due in part to the partial repopulation of grafts with endogenous cells by growth through interstices or from the anastomoses.

EXAMPLE 5

Increased Expression of tPA by Genetically Modified Canine and Human Endothelial Cells The data presented in the Examples cited above indicate that retroviral-mediated gene transfer can easily be applied to bovine, canine, and human endothelial cells. The data also indicates that it results in the proper expression of intracellular and secreted proteins. The use of retroviral-mediated gene transfer for the expression of a therapeutically relevant protein is indicated in the following section.

Tissue plasminogen activator (tPA) is a protein normally secreted by endothelial cells that promotes fibrinolysis of blood clots. Recombinant retroviral vectors encoding human tPA were constructed and used to transduce canine endothelial cells in order to demonstrate the enhanced delivery of a therapeutically relevant protein from transduced endothelial cells.

Figure 7:
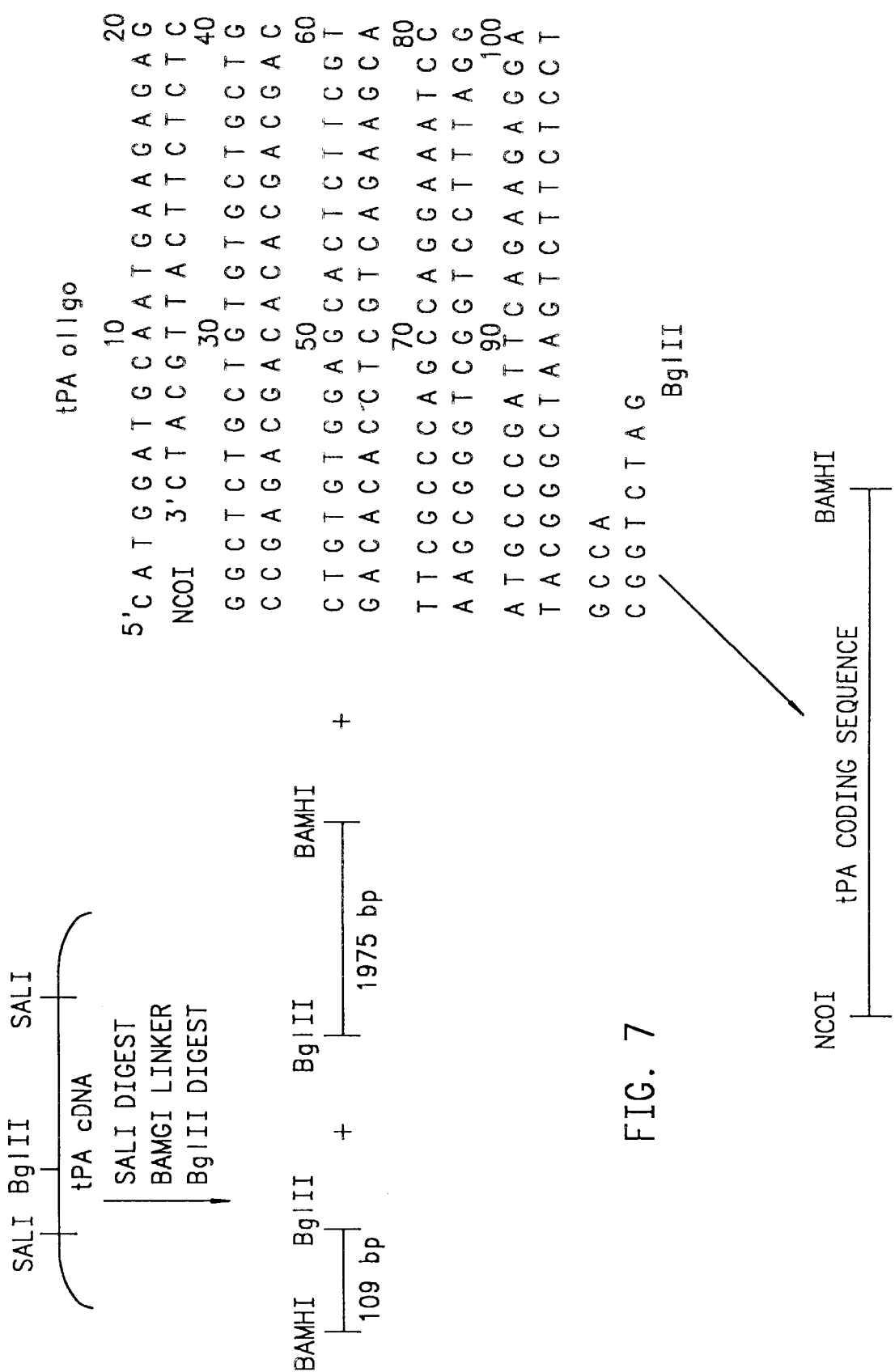
FIG. 7 is a schematic representation of the modification of the tPA gene, the oligonucleotides used to facilitate the modification and the insertion of the modified tPA gene into the vector MFG described in FIG. 2c.
Figure 8:
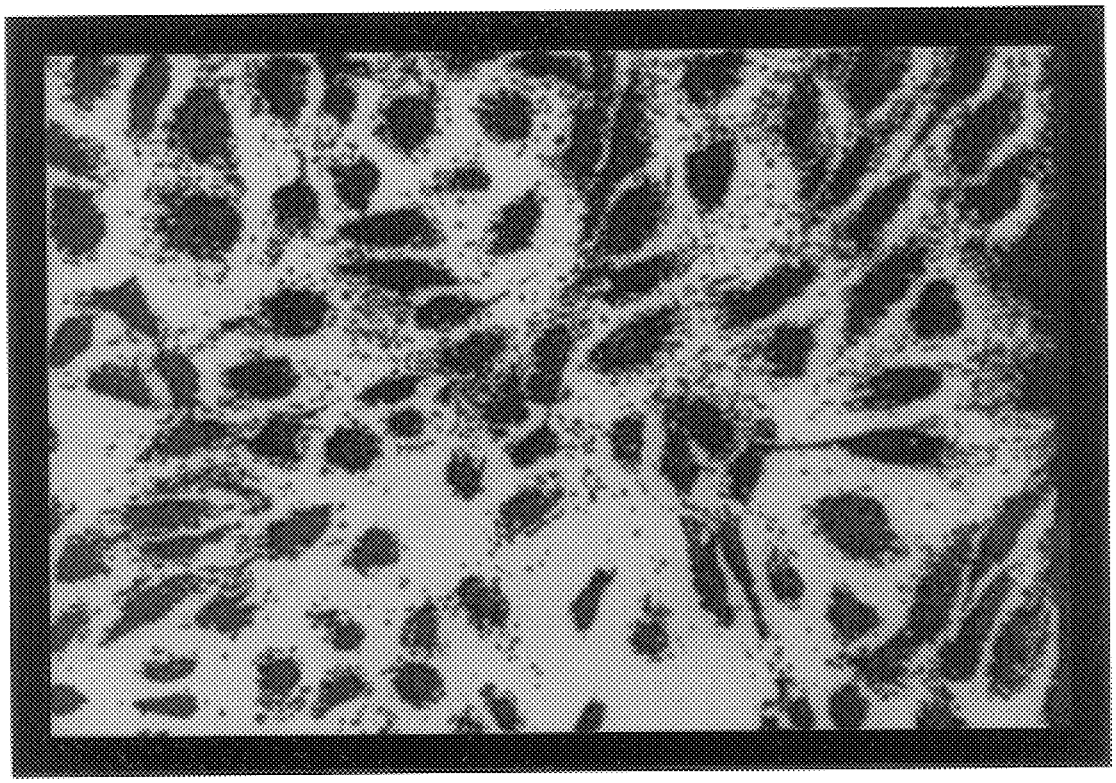
FIG. 8 is a photograph of a culture of endothelial cells identified by the expression of factor VIII-related antigen.

The modifications of the tPA gene for cloning into the recombinant retroviral vectors are shown in FIG. 7. The coding sequences of human uterine tPA were contained within a Sal I DNA fragment of a pUC-based plasmid obtained from Integrated Genetics Inc. Framingham Mass. The Sal I fragment was derived by placing Sal I linkers at the SFaN I site at base pair 6 and the Bgl II site at base pair 2090 of the original cDNA. The coding sequences extends from base pair 13 to base pair 1699.

From this original clone a fragment that could be cloned directly into the MFG and α-SCG vectors described in the body of this patent was derived. The Sal I fragment was first converted to a Bam HI fragment by the addition of synthetic Bam HI linkers and then digest with the restriction enzyme Bgl II to yield a 109 base pair Bam HI to Bgl II fragment and a 1975 base pair Bgl II to Bam HI fragment. To recreate the missing 100 base pairs of tPA coding sequences and the translational start codon, two 104 base pair oligo nucleotides were chemically synthesized and annealed to create a fragment with an Nco I site at the 5' end and a Bgl II site at the 3' end. This oligo nucleotide was ligated onto the Bgl II site of the partial 1975 base pair tPA gene to create a 2079 base pair tPA gene with the identical coding sequence of the original molecule, but which can be easily obtained as an Nco I to Bam HI fragment. It was inserted directly into the MFG and a-SGC vectors (the resulting vectors were given ATCC accession numbers 68726 and 68729, respectively).

These manipulations were performed by standard molecular biological techniques (Molecular Cloning-A laboratory Manual, T. Maniatis, E. F. Frisch, and J. Sambrook), and are diagrammed in FIG. 7.

Cell lines producing recombinant virus encoding MFG-tPA and α-SGC-tPA were made from the Psi crip packaging cell line of Danos and Mulligan capable of producing recombinant retrovirus of amphotrophic host range [Proc. Natl. Acad. Sci. U.S.A. 85:6460 (1988)]. 10 ug of the specified DNAs and 1 ug of the plasmid pSV2neo were co-precipitated and transfected onto the packaging cells by standard calcium phosphate transfection procedures. Stably transfected clones were isolated after growth for 14 days in selective media containing 800 ug/ml G418. 24 hour culture supernatants were obtained from confluent monolayers of individual clones and used to infect NIH 3T3 cells. The culture supernatants were removed after 24 hours exposure, and the 3T3 cells were refed with normal media and allowed to grow for an additional 72 hours. Fresh media was placed on these cells for 6 hours and these supernatants were assayed for human tPA with a commercially available ELISA specific for human tPA (Immunobind-5, American Diagnostica Inc., N.Y., N.Y.) From this screen, clones of the packaging cell line producing either the MFG-tPA recombinant virus or the α-SGC-tPA recombinant virus were selected and designated MFG 68 and α-SGC 22, respectively.

Canine endothelial cells were isolated from 10 cm segments of the external jugular vein by collagenase digestion as described [T. J. Hunter, S. P. Schmidt, W. V. Sharp, and (1983) Trans. Am. Soc. Artif. Intern. Organs 29:177]. The cells were propagated on fibronectin-coated tissue culture dishes in M199 media containing 5% plasma-derived equine serum, 50 ug/ml endothelial cell growth factor, and 100 ug/ml heparin. Purity of the cell cultures was determined by immunohistochemical assay for the presence of Von Willebrands Factor and the absence of smooth muscle cell specific α-actin. The day before transduction, the endothelial cells were seeded at $5.5 \times 10^3$ cells/cm$^2$ in medium without heparin. The following day, the endothelial cells were exposed for 24 hours to supernatants containing recombinant virus derived from each producer cell line to which was added 8 ug/ml polybrene. The viral supernatants were removed, the cells feed with normal media and growth was allowed to proceed for an additional 48 hours before analysis.

High molecular weight genomic DNA and total RNA were isolated from cultures of endothelial cells by standard techniques (Molecular Cloning-A Laboratory Manual T. Maniatis, E. F. Fritsch, and J. Sambrook). The DNA and RNA were analyzed by hybridization analysis with a $^{32}$P-labeled DNA probe prepared from the entire tPA cDNA fragment. Standard techniques were used for electrophoretic separation, filter transfer, hybridization, washing, and $^{32}$P-labeling (Molecular Cloning-A Laboratory Manual T. Maniatis, E. F. Fritsch, and J. Sambrook). The production of human tPA in transduced canine endothelial cells was demonstrated with a species specific immunocytochemical stain. Transduced cells were fixed in 3% formaldehyde for 10 minutes at room temperature and then permeabilized in 0.1% Triton X-100 for 5 minutes. The fixed cell monolayer was then incubated sequentially with a murine monoclonal antibody to human tPA, with an alkaline phophatase conjugated goat anti-mouse antibody, and finally with a color reagent specific for alkaline phophatase. This procedure specifically stains those cells expressing human tPA and can be visualized by conventional light microscopy. In addition, tPA secretion from transduced cells was determined from confluent cell monolayers. Fresh media was placed on the cells for 6 hours, removed and clarified by centrifugation, and the amount of human tPA determined with a commercially available ELISA (Immunobind-5, American Diagnostica).

The efficiency of the transduction process is shown by immunocytochemical stain of a population of cells mock transduced or transduced with MFG-tPA. As shown in FIG. 9, after a single exposure of the cells to a viral supernatant harvested from MFG 68, essentially all of the cells are synthesizing human tPA as opposed to none of the cells in the control. This was achieved without selection of any type for transduced cells.

An immunological assay was conducted to determine the amount of tPA that was being secreted from transduced cultures. As shown below, cells transduced with recombinant virus from either MFG 68 or α-SGC 22 secreted large amounts of human tPA. Under similar conditions, human endothelial cells in culture typically secrete approximately 1 ng of tPA [Hanss, M., and D. Collen (1987) *J. Lab. Clin. Med.* 109: 97104].

TABLE II

| Cells<br>tPA/million<br>cells/6 hours | ng human |
| --- | --- |
| uninfected K9 EC | 0.0 |
| MFG 68 K9 EC | 150.1 |
| α-SGC 22 K9 EC | 302.8 |

Figure 10:
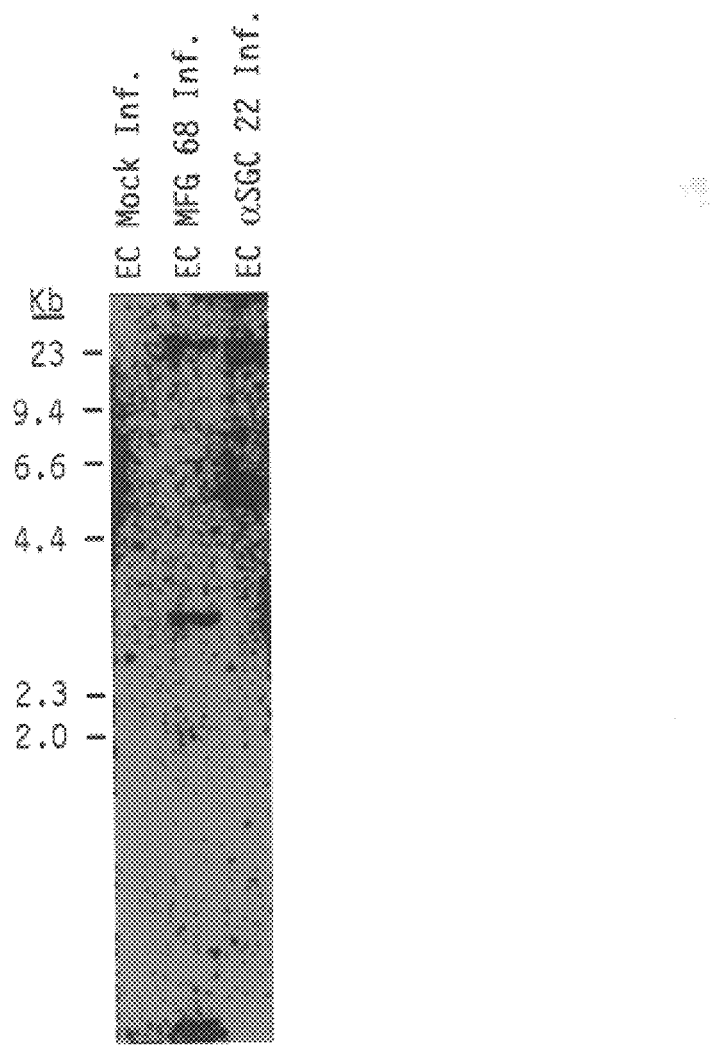
FIG. 10 is a photograph of an autoradiograph of a Southern blot of cellular genomic DNA showing the stable integration into endothelial cells of the MFG-tPA and α-SGC-tPA recombinant retroviruses.
Figure 10:
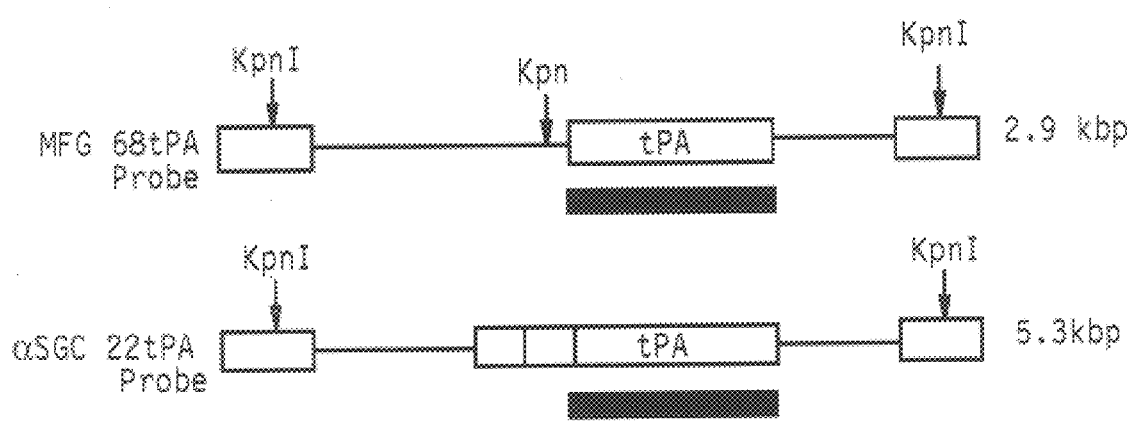

As a further confirmation that the endothelial cells had been transduced with recombinant virus from MFG 68 and a-SGC 22, DNA and RNA was isolated from transduced cells and analyzed by hybridization to a radiolabeled tPA gene. An autoradiogram of the DNA analysis is shown in FIG. 10. No hybridization was detected in the uninfected controls, but single hybridizing species of the appropriate molecular weight was seen in the cells infected with the two recombinant vectors. This demonstrates that the genetic information has been transferred to the genome of these transduced cells.

Figure 11:
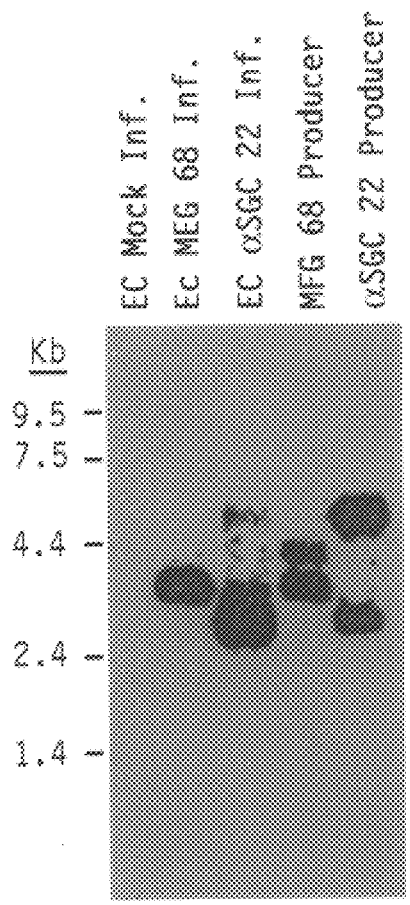
FIG. 11 is a photograph of an autoradiograph of a Northern blot of cellular RNAs showing the expression of RNAs from the MFG-tPA and α-SGC-tPA recombinant retroviruses.
Figure 11:
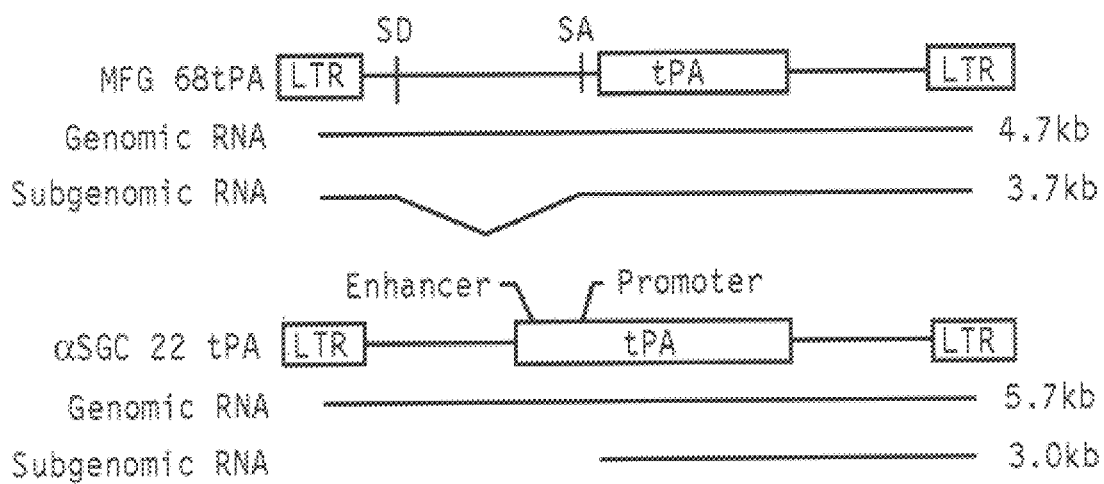

Hybridization analysis of total RNA isolated from these cells confirms the protein and DNA results and is shown in FIG. 11. Again no hybridization was detected in the control cells but in the RNA derived from the transduced cells hybridizing bands of the appropriate sizes can be seen. RNA from the MFG 68 and α-SGC 22 recombinant virus producing cells is also shown as controls.

EXAMPLE 6

In vivo Function of Transduced Canine Endothelial Cells Transplanted on the Surface of Vascular Grafts Endothelial cells were enzymatically harvested from external jugular veins of adult female mongrel dogs that weighed 20–25 kg and cultured in the laboratory and analyzed for purity as described in Example 5. One half of the cells isolated from each animal were transduced by two exposures to supernatants harvested tPafrom the MFG 68 cell line producing the MFG-tPA recombinant virus as described in the previous section. The other half were mock transduced. Growth curves conducted on each population showed no difference in growth characteristics. ELISA measurements were made on culture supernatants derived from each batch of transduced cells to assure that tPA was being secreted from the augmented cells. These cells were then propagated in the laboratory for approximately one week to obtain sufficient numbers of cells.

For each animal from which cells had been isolated, two vascular grafts made of expanded Teflon (W. L. Gore and Associates, Inc. Flagstaff, Ariz.) were seeded with cells. One graft was seeded with mock transduced cells, and the other with cells transduced to secrete high levels of tPA. Each graft, measuring 0.4 cm×14 cm, was precoated with 1.5 ug/cm$^2$ fibronectin (Sigma Chemical Corp., St. Louis Mo.), and then seeded with 2200,000 endothelial cells/cm. The grafts were then incubated for an additional 72 hours in culture. Prior to implant the ends were cut off each graft and checked to assure cell coverage.

The same dogs from which the cells had been harvested were anesthetized and 10 cm segments of the seeded grafts were implanted as aorta-iliac bypasses. Each dog received two contralateral grafts; one seeded with control cells and the other seeded with cells that had been transduced to secrete high levels of tPA. Following implantation the performance of the grafts was monitored daily with a B-mode scanner which locates the graft with ultrasound and assesses blood flow through the graft by Doppler measurements (Accuson, Inc.). No drugs to reduce thrombus formation were administered to the animals.

Figure 12:
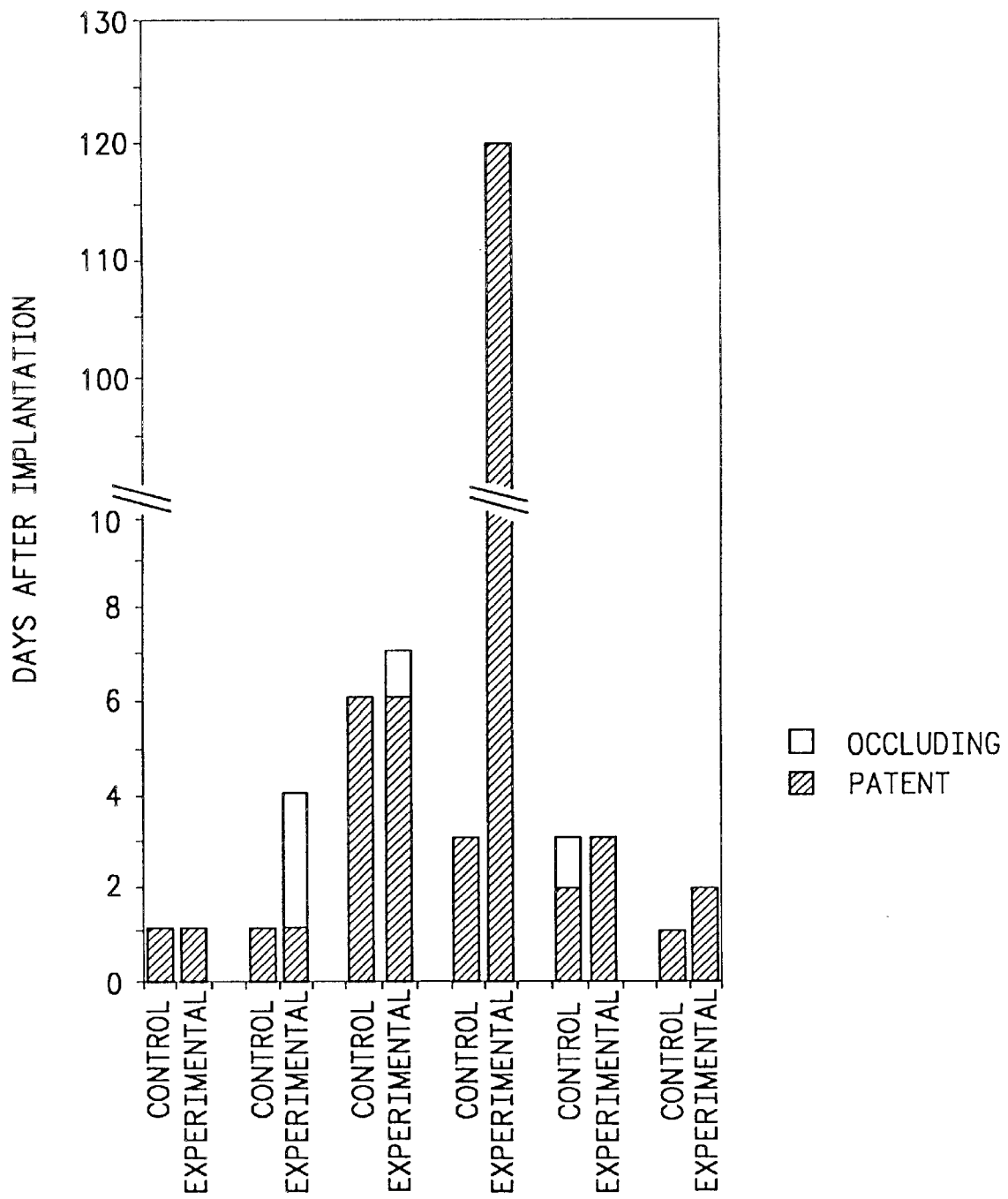
FIG. 12 is a histogram showing the potency after implantation into dogs of synthetic grafts lined with endothelial cells genetically augmented to express tPA.
Figure 13A:
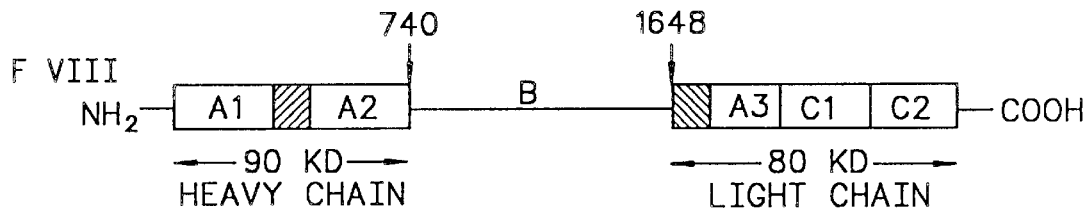
FIG. 13a is a diagram of the factor VIII polypeptide.
Figure 13B:
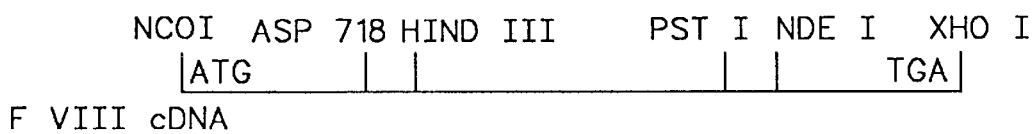
FIG. 13b is a diagram of the factor VIII cDNA showing the restriction enzyme sites used in the various constructs to generate the retroviral vector.
Figure 13C:
FIG. 13c is a diagram of the deletion derivative of the factor VIII cDNA inserted into the retroviral vector with the deleted region shown as vertical lines.
Figure 13D:
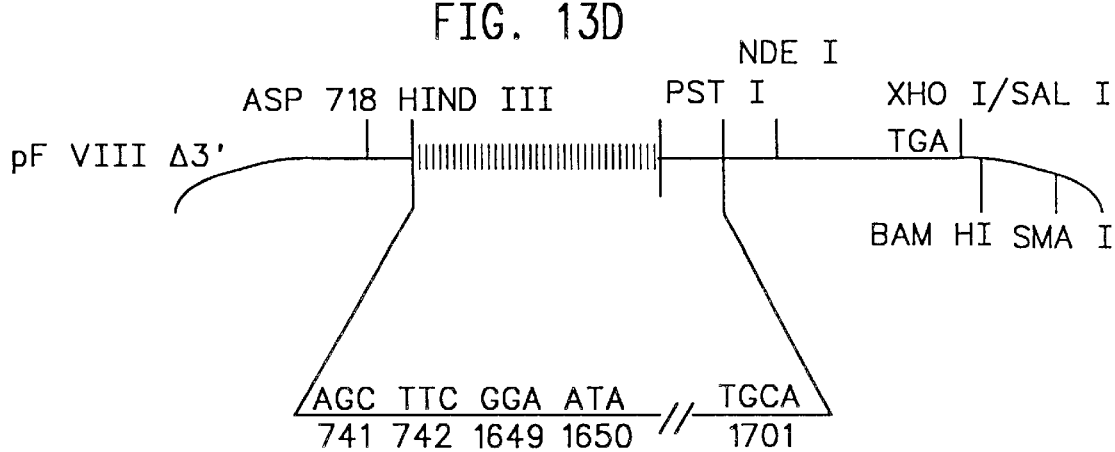
FIG. 13d is an expanded diagram of the B domain deletion between the Hind III and Pst I sites. The nucleotide sequence at the junction of the heavy chain and light chain is denoted above the line and the corresponding amino acid numbers are denoted below the line.

The results of graft performance in 6 different animals is shown in FIG. 12. The implant model described above is an extremely stringent one and leads to rapid graft failure by occlusive clot formation. Normal graft function is denoted by solid bar, and a graft which is failing but still functioning by a striped bar. In the first animal, the control graft and the graft lined with transduced cells secreting enhanced levels of tPA (experimental) failed due to clot formation 24 hours after implant. In all of the other five animals, the graft lined with transduced cells secreting enhanced levels of tPA functioned longer than the graft with cells which had only been mock transduced. This difference varied from 24 hours to several months. These results demonstrate that a therapeutic effect can be achieved in vivo with transduced endothelial cells.

EXAMPLE 7

Production of Human Factor VIII from Transduced Endothelial Cells

Endothelial cells were genetically augmented to produce human factor VIII by transducing cells with a retroviral vector, MFG, containing a modified human factor VIII gene (ATCC accession no. 68726). The modified factor VIII cDNA contains all of the coding sequences for the A1, A2, A3, C1, and C2 domains, however the B domain is deleted from amino acids 743 to 1648. The removal of the B domain and the insertion of the modified factor VIII gene into the retroviral vector MFG is described in detail below and depicted in FIG. 13.

A full-length cDNA without the 5' and 3' untranslated sequences was obtained in a plasmid vector inserted between the restriction sites Nco I (5') and Xho I (3'). For removal of the B domain, the factor VIII cDNA was subcloned into a plasmid vector in 4 fragments spanning the sequences on both the 5' and 3' sides of the B domain. The first fragment of the factor VIII cDNA was subcloned between the restriction sites Sal I and Pst I in the plasmid vector pUC 9. The plasmid vector was cut with Sal I and Pst I and the 5' phosphates were removed using calf intestinal phosphatase. A 1591 base pair Xho I (nucleotide 7263) to Nde I (nucleotide 5672) fragment, and a 359 base pair Nde I (nucleotide 5672) to Pst I (nucleotide 5313) fragment from the full-length cDNA were isolated and ligated with the Sal I/Pst I digested plasmid vector.

To remove the majority of the sequences encoding the B domain which joins amino acids 742 to 1649 in the same translational reading frame, 4 oligonucleotides were synthesized with a 5' Hind III site and a 3' Pst I site covering 168 base pairs. The oligonucleotides extend from the Hind III site at nucleotide 2427 which encodes amino acid 742 followed by amino acid 1649 which is the first amino acid of the activation peptide of the light chain through to the Pst I site at nucleotide 5313. The plasmid vector pUC 9 was digested with the restriction enzymes Hind III and Pst I, and the 5' phosphates were removed using calf intestinal phosphatase. The oligonucleotides were synthesized as 4 separate strands, kinased, annealed and ligated between the Hind III site and the Pst I site of the plasmid vector.

The subcloned Hind III/Pst I oligonucleotide was juxtaposed to the Pst I/ Xho I fragments in a plasmid vector pUC F8. To generate this plasmid, a new polylinker was inserted into a pUC 9 plasmid backbone with the new polylinker encoding the restriction enzyme sites 5' Sma I-Bam HI-Xho I-Pst I-Hind III-Asp 718-Nco I-Hpa I 3' used. The plasmid vector was digested with the restriction enzymes Bam HI and Hind III, and the 5' phosphates were removed with calf intestinal phosphatase. A partial Pst I/Bam HI digest of the Pst I/Xho I subclone was used to isolate the 3' terminal factor VIII fragment, and a Pst I/Hind III digest of the subcloned oligonucleotides was used to isolate the heavy and light chain junction fragment. They were ligated into the plasmid vector pUC F8 between the BamHI and Hind III sites.

This subclone containing the factor VIII sequences between nucleotides 2427 and 7205 was digested with Asp 718 and Hind III, and the 5' phosphates were removed using calf intestinal phosphatase. A fragment encoding factor VIII between the restriction enzyme sites Asp 718 (nucleotide 1961) and Hind III (nucleotide 2427) was isolated and ligated into the plasmid vector to generate a subclone (pF8 3' delta) containing the factor VIII sequences from nucleotide 1961 through to the translational stop codon at nucleotide 7205.

Figure 14:
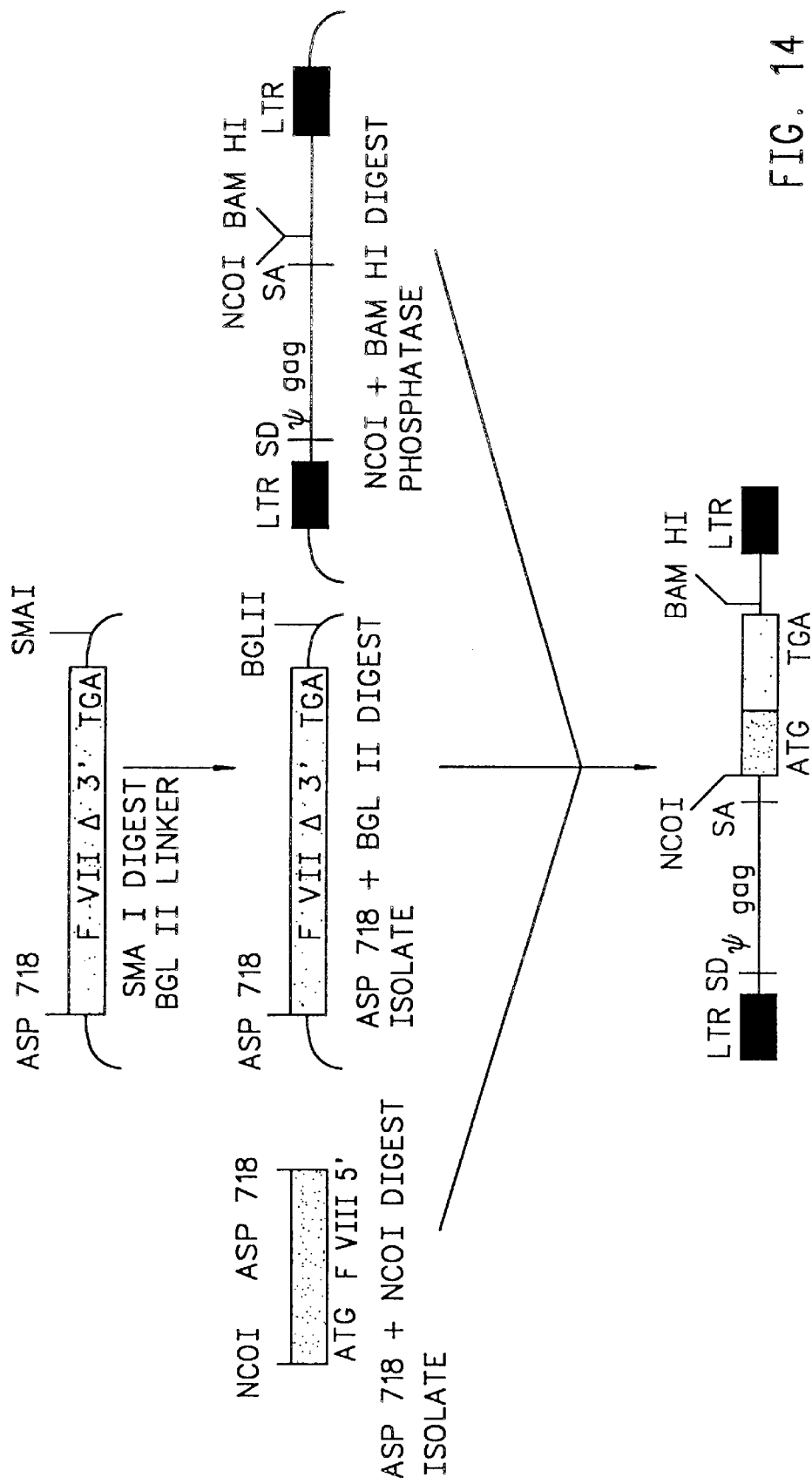
FIG. 14 is a diagram of the assembled final retroviral vector, MFG-factor VIII.

The construction of the retroviral vector containing the modified factor VIII gene was carried out by inserting the factor VIII gene between the restriction sites Nco I and Bam HI of the retroviral vector MFG. The factor VIII subclone pF8 3' delta was digested with Sma I and converted to a BglII site using an oligonucleotide linker. An Asp 718/Bgl II fragment was isolated from the 3' factor VIII subclone, and a 5' factor VIII fragment containing the ATG for initiation of translation was isolated as an Nco I (nucleotide 151)/Asp 718 fragment (nucleotide 1961). The retroviral vector MFG was digested with Nco I and Bam HI, and the 5' phosphates were removed using calf intestinal phosphatase. The factor VIII fragments were ligated into the retroviral vector yielding the final factor VIII retroviral construct, see FIG. 14.

The cell line producing the retroviral particles was generated by transfection of the retroviral vector MFG/factor VIII into equal numbers of ecotropic packaging cells Psi CRE and amphotropic packaging cells Psi CRIP as described by Bestwick et al. (Proc. Natl. Acad. Sci. USA 1988. 85:5404–5408.). To monitor the extent of superinfection taking place between the 2 host ranges of packaging cells, the production of biologically active factor VIII was measured using the Kabi Diagnostica Coatest for Factor VIII, Helena Laboratories, Beaumont, Texas and the production of viral RNA was measured by an RNA dot blot analysis. At 21 days post transfection, the mixture of transfected packaging cells was co-cultivated with the amphotropic packaging cell line Psi CRIP-HIS. The Psi CRIP HIS packaging cell line is a variant of the previously described Psi CRIP packaging cell line. The Psi CRIP HIS packaging cell line is identical to the Psi CRIP packaging cell line except that the retroviral envelop gene was introduced into the cell by cotransfection with pSV2-HIS plasmid DNA, a different dominant selectable marker gene. The packaging cell lines were cultured at a 1:1 ratio for isolation of a homogeneous amphotropic retroviral stock of transducing particles. The superinfection of the amphotropic packaging cell line Psi CRIP HIS has led to the generation of a stable cell line, HIS 19, which produces recombinant retrovirus that efficiently transduce the modified human factor VIII gene. Antibiotic selection of the retroviral producing cell line was not required to isolate a cell line which produces high-titer recombinant retrovirus. The genomic DNA of the cell line has been characterized by Southern blot hybridization analysis to determine the number of integrated copies of the retroviral vector present in the producer cell line. The copy number in the retroviral producing cell line is approximately 0.5, therefore on average 50% of the Psi CRIP-HIS packaging cells contain a copy of the retroviral vector with the modified factor VIII gene. The retroviral vector and the modified factor VIII gene are intact without any deletions or rearrangements of the DNA in the packaging cell line. The copy number of the retroviral vector remains constant with the continuous passage of the retroviral producing cell line. For obtaining the highest titer of recombinant retrovirus, HIS 19 was carried 3 passages in selective histidine minus media followed by 4 passages in completed DMEM media. For the generation of retroviral particles, HIS 19 was seeded at $5 \times 10^5 - 1 \times 10^6$ cells in a 10 cm cell culture dish. At 48 hours postseeding, approximately 70% confluency, fresh medium (DMEM+10% calf serum) was added to the plates for collection 24 hours later as the source of recombinant retrovirus for transduction.

The modified factor VIII gene was transduced into canine endothelial cells isolated from the jugular vein. The endothelial cells were seeded at 3×105 5 cells per 10 cm. dish in complete M199 medium with 5% plasma derived serum (Equine), 100 ug/ml heparin, and 50 ug/ml endothelial cell growth factor for 4–6 hours. The cells were then incubated overnight in M199 medium with 5% plasma derived serum, and 100 ug/ml endothelial cell growth factor overnight without heparin which adversely affects the efficiency of the transduction process. Cells were exposed to the fresh viral supernatant plus polybrene (8 ug/ml) for 24 hours. After removal of the viral supernatant, the cells were put into M199 medium with 5% plasma derived serum, 100 ug/ml endothelial cell growth factor to grow to approximately 70–80% confluence. At that time, the medium was changed to M199 medium with 5% heat inactivated fetal bovine serum (heated at 66° C. for 2 hours), and 50 ug/ml of ECGF. Following a 24 hr. incubation, the medium was collected and assayed for biological active factor VIII by the Kabi Coatest.

Figure 15:
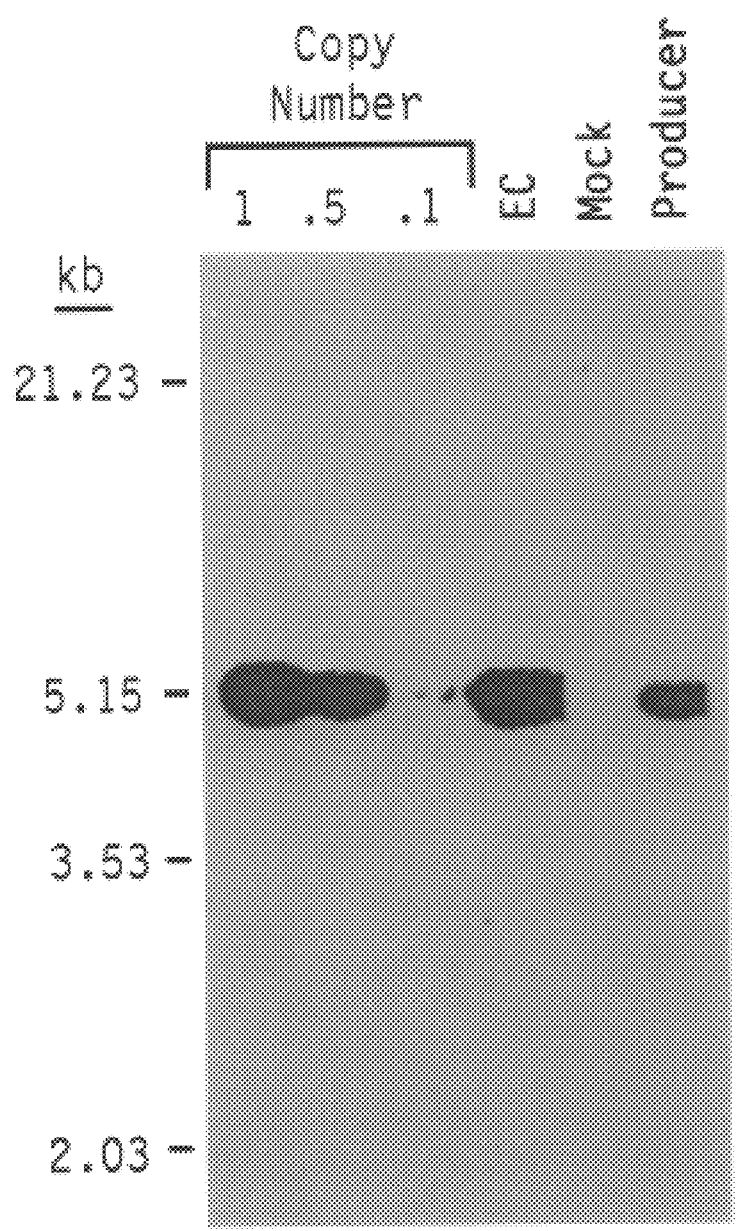
FIG. 15 is a photograph of an autoradiograph of a Southern blot of cellular genomic DNA showing the stable integration into endothelial cells of the MFG-factor VIII retrovirus.

With this retroviral producing cell line, between 50% and 75% of the endothelial cells were transduced as determined by Southern blot analysis. The factor VIII gene can be transduced at this frequency with a single exposure to the recombinant retrovirus, and without antibiotic selection of the transduced cells. The transduced endothelial cells contain an intact copy of the recombinant retroviral genome and the modified factor VIII gene without any deletions or rearrangements as shown in FIG. 15. The rate of production of biologically active factor VIII from the genetically augmented endothelial cells was 400 ng/5×10$^6$ cells/24 hrs.

EXAMPLE 8

In Vivo Transduction of the Endothelium

Using standard stocks of recombinant retrovirus made as described in the previous examples, we have obtained preliminary data demonstrating the in vivo transduction of endothelial cells. The approach is based on the previously published observation (Reidy Mass., Schwartz S. M. *Lab Invest* 44:301–308, 1981) that a defined injury to an artery surface removes a small strip of endothelial cells and this denuded area heals within seventy-two hours by proliferation and ingrowth of new endothelial cells from the edge of the defect. Cell division is a requirement for effective transduction by recombinant retroviruses and the injury of the endothelium with a wire is one of potentially many methods to induce endothelial cell proliferation. Our method uses Reidy's technique of defined injury to induce endothelial cell proliferation, then exposes the proliferating cells directly to supernatants containing recombinant retroviral vectors. Our initial experiments document the ability of this method to successfully transduce endothelial cells in situ, thus potentially avoiding the necessity of tissue culture techniques for the successful introduction of new genetic sequences.

This method requires two surgical procedures, the first procedure injures the blood vessel surface (here described for the right iliac artery) and induces the proliferation of endothelial cells. The second procedure delivers recombinant retrovirus to the cells undergoing replication on the vessel surface, while preventing the flow of blood from the proximal arterial tree while the proliferating cells are exposed to retroviral particles. For simplicity of performance the procedure is described for iliac arteries.

Figure 16:
FIG. 16 is a diagram of the a-SGC-LacZ recombinant retrovirus.
Figure 18:
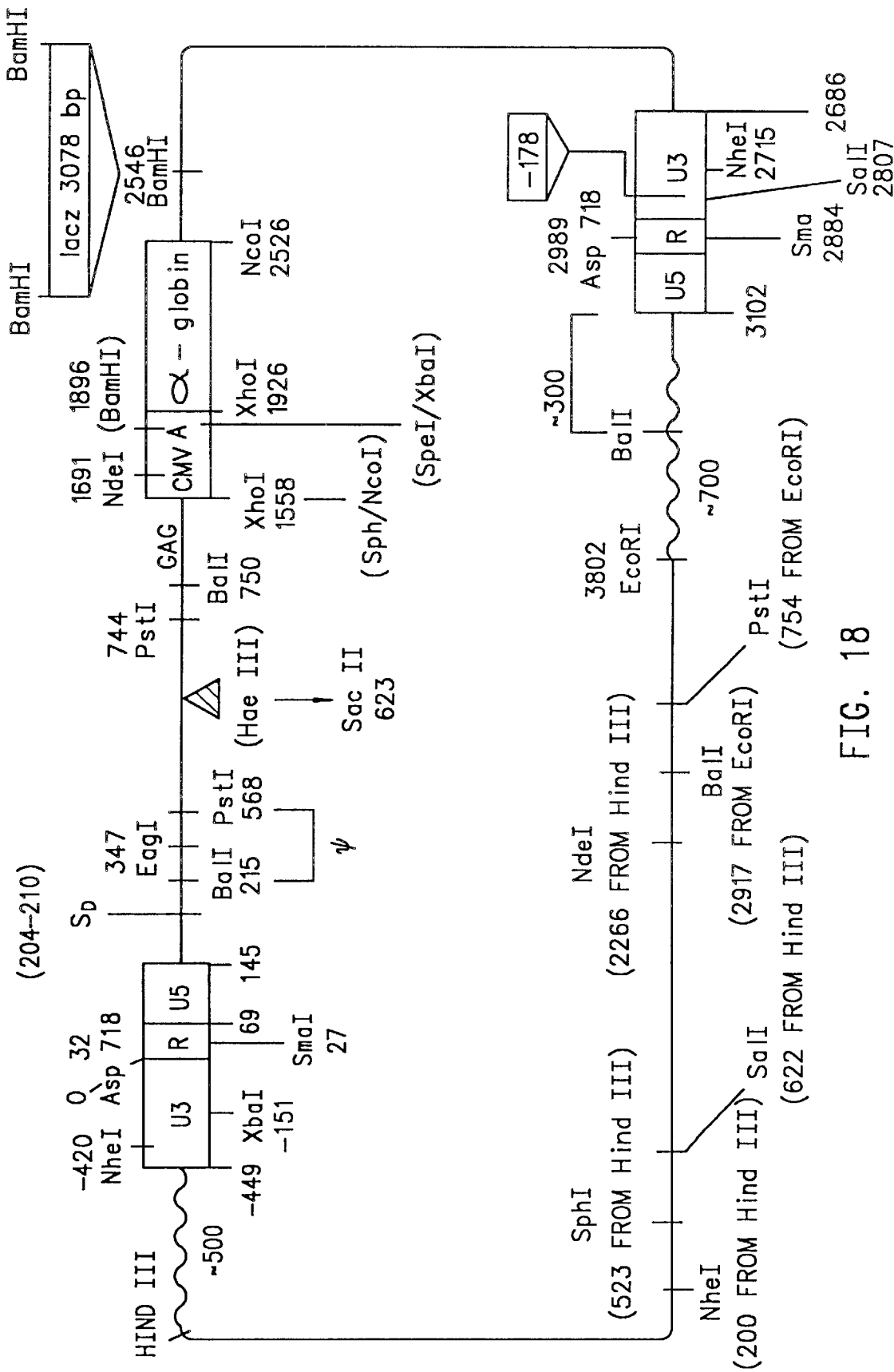
FIG. 18 is a map of retroviral vector α-SGC.

To demonstrate in vivo gene transfer, we used the marker gene concept published in 1987 (Price J, Turner D, Cepko C. 1987 *Proc. Natl. Acad. Sci.* USA 84:156–160.) (see Example 3) with an improved vector based on the α-SGC vector (FIGS. 2*d* and 18). The lacZ gene encoding beta-galactosidase was inserted into the α-SGC vector to generate the α-SGC-LacZ vector which is represented in FIG. 16. This recombinant construct was transfected into the Psi Crip packaging cell line and a clone of Psi Crip cells producing high titers of the α-SGC-LacZ recombinant retrovirus were isolated as described in Example 5. Stocks of the αSGC-LacZ recombinant retrovirus were used for in vivo transduction.

The experimental animals (rabbit) were anesthetized (ketamine/xylazine), both groins were shaved and prepped, and the animals positioned on an operating table. Through bilateral vertical groin incisions the common, superficial, and profunda femoral arteries were exposed. On the right (the side to be injured) small branches off the common femoral artery were ligated to insure that outflow from the isolated arterial segment would only occur through the internal iliac artery. If necessary, the inguinal ligament was divided and the vessel followed into the retroperitoneum to assure complete control of all side branches. The right superficial femoral artery (SFA) was ligated with 3-0 silk approximately 1.5 cm below the profunda take-off, control of the SFA was obtained at the SFA/profunda junction, and a transverse arteriotomy created. A fine wire (the stylet of a 20 gauge Intracath was used), doubled upon itself to provide springiness to assure contact with the vessel wall, was passed up the common femoral and iliac artery retrograde to produce the defined injury described by Reidy et al. The wire was removed, a 20 gauge angiocath was inserted in the arteriotomy and secured to the underlying muscle for immediate access at the next surgical procedure. The incisions were closed in layers and the animals allowed to recover.

Twenty-four hours later a recombinant virus containing supernatant harvested from a crip producer of the αSGC-LAC-Z vector and supplemented with polybrene to a final concentration of 8 ug/ml was used for in vivo transduction. The animals were again anesthetized and both incisions reopened in a sterile environment. To obtain control of the right iliac vessels above the area that had been injured with no disturbance to the previously denuded right iliac vessel, a #3 Fogarty™ balloon embolectomy catheter was inserted through an arteriotomy in the left superficial femoral artery, passed to the aortic bifurcation and the balloon inflated to interrupt blood flow. The right profunda femoris artery was occluded. The supernatant (10 ml) containing the recombinant retrovirus was introduced by hand injection through the angiocath previously placed in the right SFA. The supernatant flowed in a retrograde fashion from the right common femoral to the right external iliac and into the right internal iliac artery. By leaving the right internal iliac artery open outflow for the supernatant was allowed and a full 10 ml of supernatant could be instilled. In the experiments performed to date the supernatants have been exposed to the vessel wall for periods of four to eight minutes. The catheters from the left and right sides were then removed, hemostasis obtained, and the incisions closed.

Ten to fourteen days later animals were anesthetized prior to sacrifice. After anesthesia and prior to exposure, patency was assessed by direct palpation of the distal vessel. The infra-renal aorta and inferior vena cava were surgically exposed, cannulated, and the vessels of the lower extremity flushed with heparinized Ringer's lactate (2 U/ml) at physiologic pressure (90 mmhg.). A lethal dose of nembutal was administered and the arteries perfusionfixed in situ in 0.5% gluteraldehyde in 0.1 M cacodylate for 10 minutes. The aorta and both iliac arteries were excised in continuity and rinsed in phosphate buffered saline (PBS) with 1 mM MgCl2. The vessels were then stained for lacZ activity by incubation in the x-gal substrate for 1–1.5 hours at 37° C. When the reaction was complete, the x-gal solution was washed away and replaced with PBS, photographed and shown in FIG. 17.

Figure 17A:
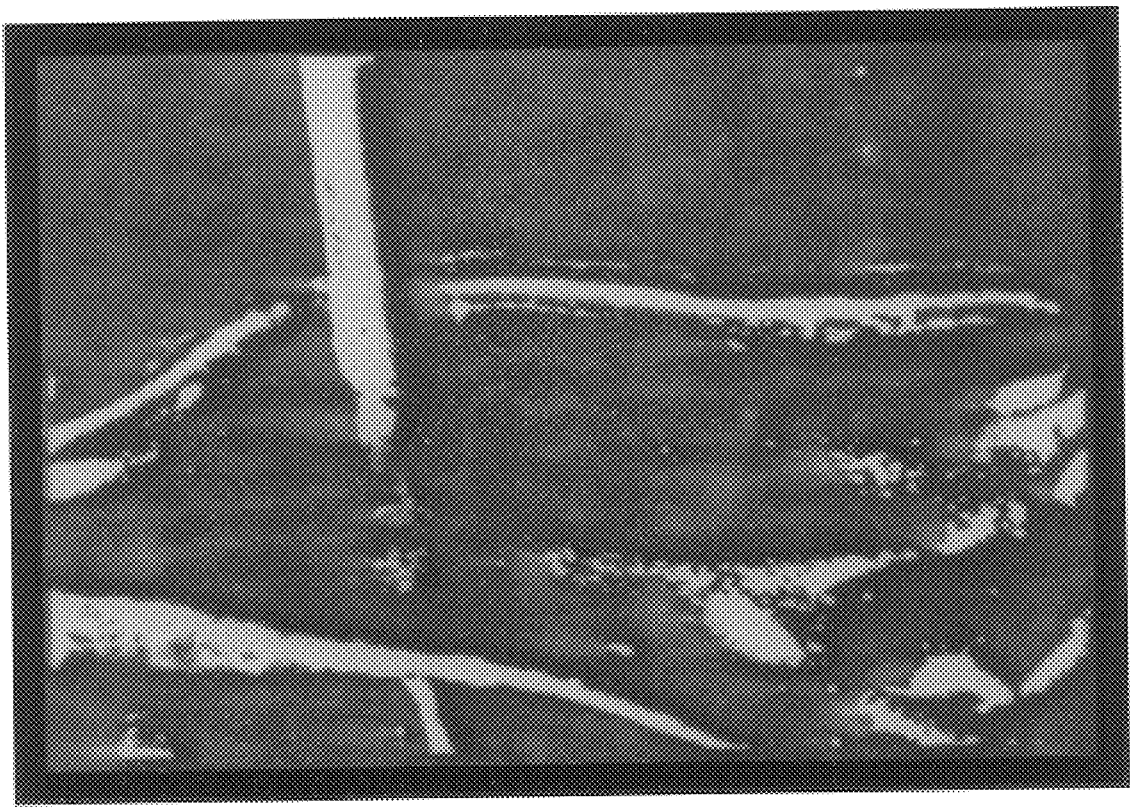
FIG. 17a is a low magnification photograph of an artery transduced in vivo with the α-SGC-LacZ retrovirus.
Figure 17B:
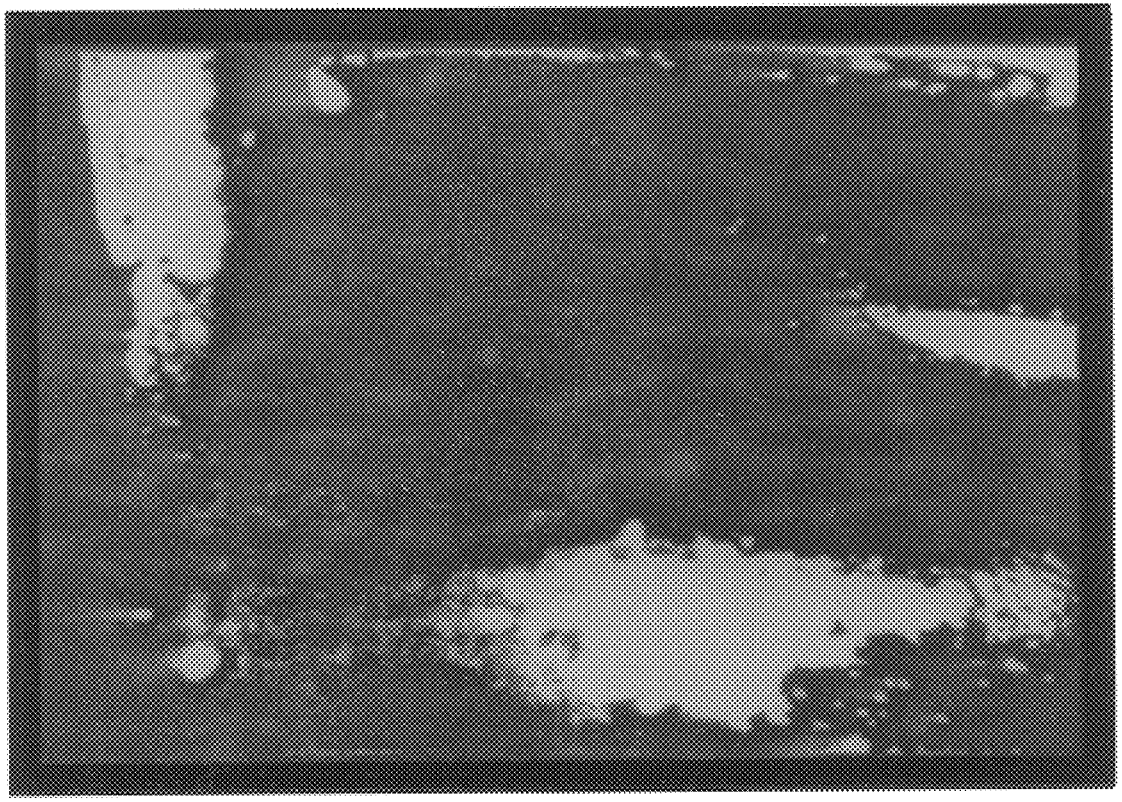
FIG. 17b is a high magnification photograph of the same.
Figure 17C:
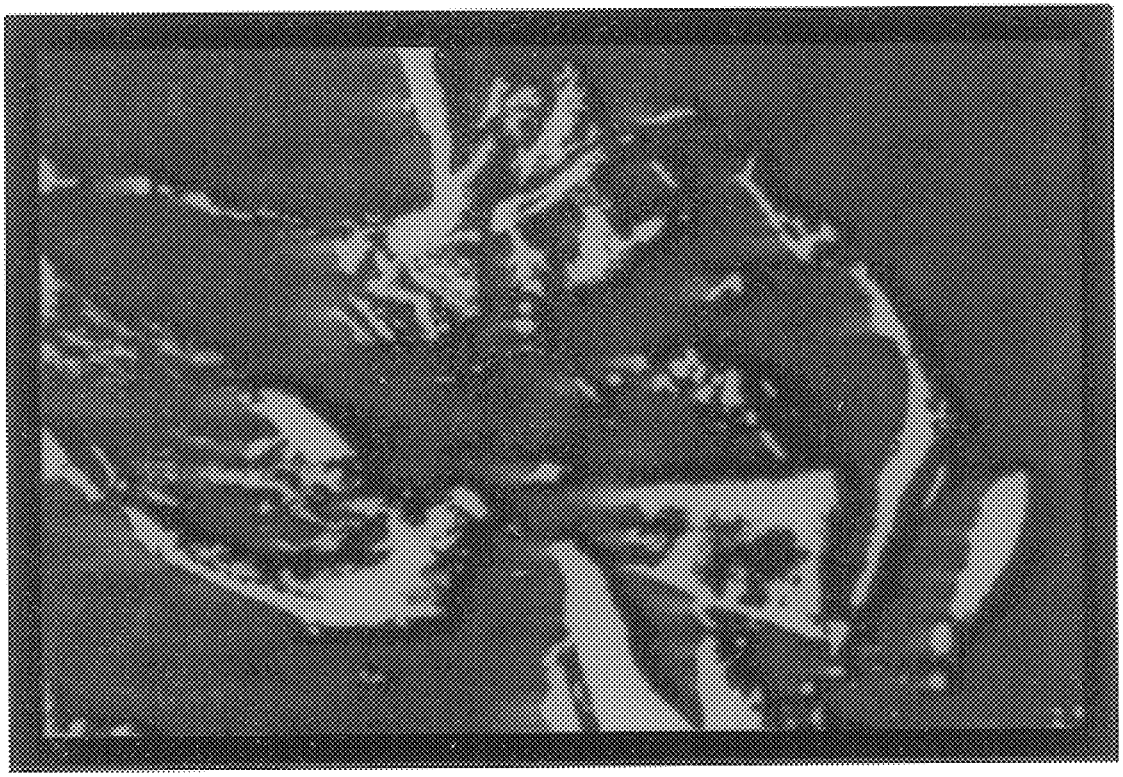
FIG. 17c is a segment of nontransduced artery.

Two experiments have been completed with this protocol. Both experiments demonstrated successful in vivo transduction as shown by the in situ expression of the lacZ gene product in cells on the surface of the artery as visualized by the selective intense blue staining in a cytoplasmic pattern (FIG. 17). FIGS. 17A and B is a segment of the external illiac artery injured with a wire, exposed to αSGC-LacZ recombinant retrovirus, fixed and stained for lacZ activity and photographed with low magnification (FIG. 17A) and high magnification (FIG. 17B). Note the line of intensely stained blue cells consistent with the pattern of injury and proliferation described by Reidy et al. FIG. 17 C is a photograph at low magnification of the same artery distal to the site of virus injection which has been identically fixed and stained. This area has only modest and diffuse background staining.

Biological Deposits

On Oct. 3, 1991, Applicants have deposited with the American Type Culture Collection, Rockville, Md., USA (ATCC) the plasmid MFG with the factor VIII insertion, described herein ATCC accession no. 68726, plasmid MFG with the tPA insertion, described herein, given ATCC accession no. 68727, the plasmid A-SGC, described herein, with the factor VIII insertion, given ATTC ascession no. 68728, and plasmid t-SGC with the tPA insertion, described herein, given ATCC accession no. 68729. On Oct. 9, 1991, Applicants have deposited with the American Type Culture Collection, Rockville, Md., USA (ATCC) the plasmid MFG, described herein, given ATCC accession no. 68754, and plasmid α-SGC, described herein and given ATCC accession no. 68755. These deposits were made under the provisions of the Budapest Treaty on the International Recognition of the Deposit of Microorganisms for the purposes of patent procedure and the Regulations thereunder (Budapest Treaty). This assures maintenance of a viable culture for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

Equivalents

Those skilled in the art will recognize, or be able to ascertian using no more than routine experimentation, many equivalents to the specific embodiments of the invention described specifically herein. Such equivalents are intended to be encompassed in the scope of the following claims.

We claim:

1. A method of reducing the thrombogenicity of a synthetic prosthetic vessel, comprising applying to the vessel endothelial cells transduced with genetic material encoding a thrombolytic protein.

2. A method of claim 1 wherein the genetic material encodes tissue plasminogen activator or streptokinase.

3. A method of using transduced endothelial cells which express incorporated genetic material of interest, comprising the steps of:

a) contacting cultured endothelial cells with media containing an infectious recombinant retrovirus having a recombinant genome comprising the genetic material of interest;

b) maintaining the cultured endothelial cells with media containing an infectious recombinant retrovirus under conditions appropriate for infection of the endothelial cells by recombinant retrovirus;

c) lining the inner surface of a prosthetic vessel with the endothelial cells infected in (b) under conditions appropriate for maintenance of the endothelial cells; and d) introducing the prosthetic vessel formed in (c) into a mammal.

4. A method according to claim 3 wherein said genetic material encodes a thrombolytic protein.

5. A method according to claim 3 wherein said recombinant retrovirus is derived from a retroviral vector selected from the group consisting of α-SGC and MFG.

6. A method according to claim 4 wherein said thrombolytic protein is tissue plasminogen activator or streptokinase.

* * * * *